(12) United States Patent
Dharmadhikari et al.

(10) Patent No.: US 9,642,811 B2
(45) Date of Patent: *May 9, 2017

(54) ABUSE DETERRENT IMMEDIATE RELEASE BIPHASIC MATRIX SOLID DOSAGE FORM

(71) Applicant: SUN PHARMA ADVANCED RESEARCH COMPANY LTD., Mumbai (IN)

(72) Inventors: Nitin Bhalachandra Dharmadhikari, Mumbai (IN); Yashoraj Rupsinh Zala, Mumbai (IN); Dilip Shanghvi, Mumbai (IN)

(73) Assignee: SUN PHARMA ADVANCED RESEARCH COMPANY LTD., Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/667,826

(22) Filed: Mar. 25, 2015

(65) Prior Publication Data

US 2015/0272902 A1    Oct. 1, 2015

(30) Foreign Application Priority Data

Mar. 26, 2014 (IN) .......................... 1041/MUM/2014
Jul. 23, 2014 (IN) .......................... 2378/MUM/2014
Sep. 13, 2014 (IN) .......................... 2917/MUM/2014
Jan. 8, 2015 (IN) ............................. 74/MUM/2015

(51) Int. Cl.
| | | |
|---|---|---|
| A61K 9/28 | (2006.01) | |
| A61K 9/48 | (2006.01) | |
| A61K 31/137 | (2006.01) | |
| A61K 31/5517 | (2006.01) | |
| A61K 9/20 | (2006.01) | |
| A61K 31/433 | (2006.01) | |
| A61K 9/50 | (2006.01) | |

(52) U.S. Cl.
CPC .......... *A61K 9/2846* (2013.01); *A61K 9/2009* (2013.01); *A61K 9/2027* (2013.01); *A61K 9/2081* (2013.01); *A61K 9/4808* (2013.01); *A61K 31/137* (2013.01); *A61K 31/433* (2013.01); *A61K 31/5517* (2013.01); *A61K 9/5026* (2013.01)

(58) Field of Classification Search
None
See application file for complete search history.

(56) References Cited

U.S. PATENT DOCUMENTS

| | | | | |
|---|---|---|---|---|
| 2006/0105038 A1* | 5/2006 | Lai | .......... | A61K 9/0056 424/470 |
| 2008/0069878 A1* | 3/2008 | Venkatesh | .......... | A61K 9/5026 424/468 |
| 2014/0155388 A1* | 6/2014 | Brzeczko | .......... | A61K 31/5517 514/220 |

OTHER PUBLICATIONS

Kollicoat Smartseal 30 D Technical Information, Jun. 2011, pp. 1-16.*

* cited by examiner

*Primary Examiner* — Abigail Fisher
(74) *Attorney, Agent, or Firm* — Sughrue Mion, PLLC

(57) ABSTRACT

An abuse deterrent immediate release biphasic matrix solid dosage form that releases the drug at a desired rate for quick onset of action when a single unit or prescribed units of the dosage form are orally administered but exhibits a reduced rate of release when more than the prescribed number of units, are administered.

7 Claims, 11 Drawing Sheets

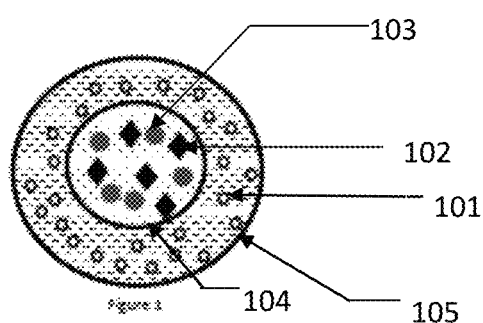
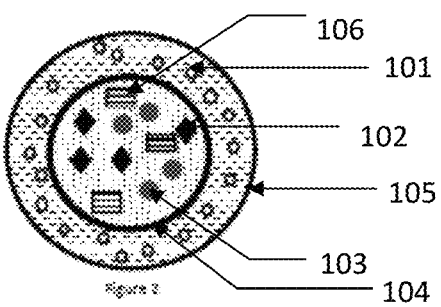
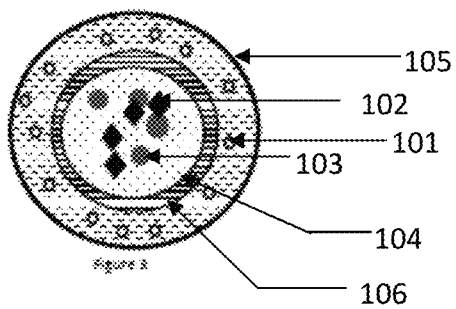

ABUSE DETERRENT IMMEDIATE RELEASE BIPHASIC MATRIX SOLID DOSAGE FORM

BACKGROUND OF THE INVENTION

1. Field

The present invention relates to abuse deterrent immediate release biphasic matrix solid dosage that releases the drug at a desired rate for quick onset of action when a single unit or prescribed units of the dosage form are orally administered but exhibits a reduced rate of release when more than the prescribed number of units, are administered. When an abuser, with the objective of achieving a high blood concentration of the drug uses multiple units of the dosage forms through multiple modes of abuse such as extraction or ingestion, he encounters resistance of the dosage form to release high amounts of the drug and provide high blood concentration.

Abuse of prescription drugs is considered an epidemic. Abuse of the prescription behavior may be for satisfying the craving for an addictive drug. It may be for improvement of performance such as use of steroids and stimulants. Prescription drugs may also be abused for abetting suicides by taking multiple pills.

An abuser of prescription drugs seeking to satisfy the craving for an addictive drug such as opioids, seeks a potent and rapid "high" i.e. euphoria and this is obtained by achieving a high blood concentration (high "$C_{max}$") in a short time ($T_{max}$) (Katz et al (The American Journal of Drug and Alcohol Abuse, 37:205-257, 2011, Abreu, M. E., G. E. Bigelow, L. Fleisher, S. L. Walsh, 2001, Effect of Intravenous Injection Speed on Responses to Cocaine and Hydromorphone in Humans, *Psychopharmacology*, 154:76-84; de Wit, H., B. Bodker, J. Ambre, 1992, Rate of Increase of Plasma Drug Level Influences Subjective Responses in Humans, *Psychopharmacology*, 107:352-358; and de Wit, H., S. Didish, J. Ambre, 1993, Subjective and Behavioral Effects of Diazepam Depend on Its Rate of Onset, *Psychopharmacology*, 112: 324-330). Extended release dosage forms provide peak plasma concentration at a longer time ($T_{max}$) but because they are given at a lower frequency for example once-a-day they contain a higher amount of drug than immediate release or rapid release dosage forms. Therefore, they are attractive to the abuser when the abuser can tamper with them to destroy the controlled release properties. Thus, one-way to deter misuse is to provide the medication in an extended release form together with design features such as tamper resistance that prevent the abuser from defeating the controlled release properties or extracting the opioid from the dosage form in aqueous or organic liquids. In April 2013, USFDA refused to approve generic versions of Oxycontin extended release formulations that were not tamper-resistant and thus susceptible to abuse. Therefore it is essential to have design features that prevent the abuser from taking a prescription dosage form and tampering it to produce a form suitable for achieving a high $C_{max}$ in a short time ($T_{max}$) through oral administration or administration via fast onset routes such as parenteral or nasal. Commonly the extended release dosage form is indicated for chronic therapy, for example, opioid extended release formulations are indicated for pain severe enough to require daily around-the-clock treatment. Technology for such tamper resistant dosage forms has been available for more than a decade and has been used in recently commercialized opioid products such as Oxcontin® ER Tablets (containing oxycodone hydrochloride as the active ingredient). Examples of such abuse deterrent dosage forms are described in U.S. Pat. Nos. 6,488,963, 7,776,314, 8,114,383, 8,309,060, 8,337,888, 8,075,872, 8,114,384, 8,192,722, 8,420,056, 8,507,001 and 8,298,581.

However, rapid release opioids are also required and are prescribed by physicians when a quick onset of action is needed. For example, Oxcontin® ER Tablets are available in strengths of 10, 15, 20, 30, 40, 60 and 80 mg of oxycodone base, whereas immediate or rapid release Oxycodone Tablets are available in strengths of 5, 7.5, 10, 15, 20 and 30 mg of oxycodone. In view of the liking for a high $C_{max}$ and in view of development of tolerance, chronic abusers graduate to higher and higher dosages of the opioid. Therefore chronic abuser generally requires multiple doses of an immediate or rapid release dosage form. Therefore, dosage forms that release a drug susceptible to abuse rapidly may be subject to abuse by administration of multiple pills.

In addition to opioids, multiple dosage forms of antidepressants, antipsychotic and other CNS drugs are also widely abused in suicidal attempts. Overdose refers to ingestion of a dose greater than a usual dose. "Usual dose" as used herein means a dose approved by a drug regulatory authority such as Food & Drug Administration or prescribed by a physician for treatment or prevention of a diseases condition or relief of symptoms thereof. The high plasma levels of a drug candidate resulting from the overdose, causes adverse effects often leading to medical emergency and inconvenience to his or her family and the medical profession involved. Death is often a consequence of serious overdosing. A person's tolerance to overdose varies with age, state of health, how the substance was consumed and other factors. Death may follow immediately or more slowly if organs are permanently damaged.

A patient may ingest an overdose accidentally or through intentional misuse. In case of accidental overdose, a person takes a wrong drug or combination of drugs, in the wrong amount or at the wrong time inadvertently. On the other hand, in case of intentional misuse, a person takes an overdose to get 'high' or to inflict self-harm. The latter may be a cry for help or a suicide attempt.

Use of medication is increasing world-wide. The United States Food and Drug Administration (USFDA) has approved more than 10000. The reasons may be the introduction of vast number of agents by the advanced pharmaceutical industry in addition to the wide spectrum of diseases that increased demands for intensifying therapeutic challenges. Most commonly, the patient benefits from pharmacotherapeutic interventions; however, adverse events, ranging from minor side effects to death, may occur. Any deviation from the intended beneficial effect of a medication results in a drug related problem (DRP). (Al-Arifi et al., *Saudi Pharmaceutical Journal*, January 2014, 22(1), 17-25).

It has been estimated that DRPs account for 17 million emergency department (ED) visits and 8.7 million hospital admissions annually in the United States. (Johnson et al., *Archives of Internal Medicine*, October 1995, 155(18), 1949-56) Between 1995 and 2000, a probability model estimated that costs associated with morbidity and mortality secondary to DRPs have more than doubled from US$76.6 billion to more than US$177.4 billion. (Ernst et al., *Journal of American Pharmacists Association*, 2001 March-April, 41(2), 192-9). In United States of America, estimates on drug-related visits to hospital emergency departments (ED) are obtained from the Drug Abuse Warning Network (DAWN), which is a public health surveillance system managed by the Substance Abuse and Mental Health Services Administration (SAMHSA), U.S. Department of Health and Human Services (HHS). The DAWN database as updated till 2011 and it reports more than 500 different medications being reported to be consumed accidentally leading the user to make emergency visits. Out of these different medications, the majority of the drugs being overdosed causing emergency situations are mainly, antidepressants, analgesics, hypnotics and sedatives (http://www.samhsa.gov/data/).

One or more DRPs may develop in a given patient after the initial drug therapy. Although many DRPs can be resolved without a major impact on patient's health, some of them can be associated with significant morbidity and mortality. (Classen et al., *Journal of American Medical Association*, January 1997, 277 (4), 301-6). Hepler et al defined DRP as an event or circumstance involving drug treatment that actually or potentially interferes with the patients experiencing an optimum outcome of medical care. They also classified DRPs into eight general categories, which include untreated indication, treatment without indication, improper drug selection, too little drug, too much drug, noncompliance, adverse drug reaction (ADR), and drug interaction (Hepler et al., *American Journal of Hospital Pharmacy*, 1990 March, 47(3), 533-43).

The most common class of drugs reported in literature that cause drug related problems due to intention or unintentional overdose are tricyclic antidepressants (TCS), benzodiazepines, analgesics like paracetamol, aspirin and opioids.

Kerr et al. reviewed the overdose because of tricyclic antidepressants. Overdoses of tricyclic antidepressant are among the commonest causes of drug poisoning seen in accident and emergency department. Complications of tricyclic antidepressant overdose reported were sinus tachycardia, ECG changes, Heart block, Vasodilatation, Hypotension, Cardiogenic shock and Ventricular fibrillation. CNS related complications include Drowsiness, Coma, Convulsions, Pyramidal signs, Rigidity, Delirium, Respiratory depression, Ophthalmoplegia. Different anticholinergic effects observed were Dry mouth Blurred vision, dilated pupils, Urinary retention, absent bowel sounds, Pyrexia, Myoclonic twitching. (Kerr et al., *Emergency Medicine Journal*, 2001, 18, 236-241).

As reported, 20% of deaths were associated with accidental deaths due to overdose whereas 80% were associated with intentional deaths, suggesting that most deaths from antidepressant drugs are due to suicide. Tricyclic antidepressants are associated with a higher number of accidental and intentional deaths, and significantly more accidental (P50.0001) and intentional (P50.001) deaths were observed with the tricyclics than would be expected when standardized for the number of prescriptions. The SSRIs were associated with significantly fewer accidental (P50.0001) and intentional (P50.0001) deaths than would be expected when standardized for the number of prescriptions. For the other antidepressant drugs there was no significant difference (Survjit cheeta et al., *British journal of Psychiatry*, 2004, 184:41-47). Therefore SSRI (selective serotonin reuptake inhibitors) are considered to be less toxic than in overdose than TCA (tricyclic antidepressants). Venlafaxine a SSRI was studied. (Whyte et al., *Quarterly journal of medicine*, 2003, 96, 369-374)

Benzodiazepines are among the most frequently prescribed drugs worldwide. This popularity is based not only on their efficacy but also on their remarkable safety. Pure benzodiazepine overdoses usually induce a mild to moderate central nervous system depression; deep coma requiring assisted ventilation is rare, and should prompt a search for other toxic substances. The severity of the CNS depression is influenced by the dose, the age of the patient and his or her clinical status prior to the ingestion, and the congestion of other CNS depressants. In severe overdoses, benzodiazepines can occasionally induce cardiovascular and pulmonary toxicity, but deaths resulting from pure benzodiazepine overdoses are rare. (Gaudreault P. et al., *Drug Safety*, 1991 July-August, 6(4), 247-65).

It has been reported that between 1993 and 2004, 2,196 poisoning deaths occurred involving paracetamol. Overdose is one of the most frequent indications for patients to be admitted to the medical wards. In the recent past, three changes have occurred which might influence self-poisoning. First, a change in available paracetamol packs size. Secondly, the introduction of new antidepressant drugs some of which, in particular the SSRI group, are perceived as being less toxic in overdose, has resulted in a more than two-fold increase in prescriptions. Thirdly an in increasing use of drugs of abuse, specifically opiates, which is itself associated with an increase in self-harm and suicide. (Bateman et al., *Quarterly Journal of Medicine*, 2003, 96, 125-132).

According to Bohmert et. al, there was increase in rate of unintentional overdose in USA by 124% largely because of the prescription opioids. Higher prescribed doses increase the risk of drug overdose among individuals treated with opioids for chronic non-cancer pain (Bohmert et al., *The journal of the American medical association*, 6 Apr. 2011, vol 305, No. 13).

It is estimated that 52% deaths were caused due overdoses of anticoagulants, insulin and oral hypoglycemic, cardiac glycosides or thyroxine out of which 50% were accidental (D Gunnell et al., *Emergency Medicine Journal*, 2004, 21, 35-38).

Brune et all report that aspirin and paracetamol are lethal when taken at overdose. They are best-selling OTC drugs and can pose a significant risk to the consumer who is unaware of the toxicity of these drugs (Brune et al., *Current Rheumatology Reports February*, 2009, Volume 11, Issue 1, 36-40).

For reasons discussed hereinabove, particularly preventing intentional abuse for addiction or suicidal attempt or unintentional/accidental overdosing. there is a need for an abuse deterrent solid dosage form that allows the release of the drug at a desirable rate when a single or prescribed number of units of the dosage form are orally administered but exhibits a reduced rate of release when more than single unit or prescribed number of units, are simultaneously orally administered. The present inventors have discovered biphasic matrix solid dosage forms that can resolve at least one of the modes of abuse of immediate release solid dosage form such as a. intentional abuse of overdosing or multiple unit administration by an addict or by a subject having suicidal intention, b. intentional abuse of extraction from multiple unit administration by an addict or by a subject having suicidal intention c. unintentional or accidental overdosing, d. concomitant alcohol consumption and resultant drug-alcohol interaction e. intentional abuse by nasal, parenteral, rectal or oral route f. separating two phases by physical means with an intention to abuse Particular embodiments have been discovered that simultaneously resolve two or three or more of the above modes of abuse. Further embodiments of biphasic matrix solid dosage forms have been discovered that are resistant to physical means for separating the two phases with an intention to abuse. The physical means may be crushing the dosage form followed by size separation.

SUMMARY OF THE INVENTION

The abuse deterrent immediate release solid biphasic matrix dosage form of the present invention comprises a drug susceptible to abuse and a release inhibiting agent such that when more than the prescribed number of units of the dosage form are orally administered, the release is inhibited as compared to the release when a single unit of the dosage form is orally administered. The term 'release inhibiting agent' as used herein refers to a substance or a combination thereof, that functions to inhibit the release of the drug susceptible to abuse in gastric fluids only when more than the prescribed number of units of the dosage form are orally administered. In preferred embodiment, the release inhibiting agent is a combination of one or more reverse enteric polymers and an antacid. The release inhibiting agent either fails to have a significant effect of inhibiting the release when a single unit of the dosage form is orally administered or has no effect. In this way the dosage form of the present invention is useful to deter the abuse of drugs by drug addicts or by individuals seeking to commit suicide. In certain embodiments, where the prescribed number of units of the immediate release of the solid dosage form of the present invention is two, then the composition of the release inhibiting agent used is such that the two prescribed number of units provide the release of the drug which is equivalent to the release obtained from the conventional, immediate release solid dosage form. But, when three or more number of units is tested, the release is inhibited as compared to the equivalent number of units of the conventional immediate release solid dosage form. It is observed that as the number of units of the immediate release solid dosage form of the present invention increases, release rate decreases. This will provide deterrence particularly, against misuse, intentional such as suicidal (overdose) or unintentional, or abuse by an abuser or addict.

The present invention provides an abuse deterrent immediate release biphasic matrix solid dosage form that deters the abuse of the drug by multiple pill oral administration as well as abuse by other routes of administration such as nasal, parenteral and rectal.

The present inventors have discovered that certain preferred embodiments of the present invention can provide very high resistance to multiple pill abuse. Particularly they have discovered the preferred mode of incorporating the antacid such as an alkalizer. When a part of the antacid is in the same phase as the reverse enteric polymer i.e in admixture with each other, the combination forms a highly effective release inhibiting agent. Also particularly the present inventors have discovered release inhibiting combination of an antacid and a reverse enteric polymer that is soluble in acidic solutions but insoluble above second higher pH value and insoluble above a second higher pH value is surprisingly advantageous as compared to the reverse enteric polymer that is soluble in acidic solutions but which swells or gels above a second higher pH value. When multiple pills are taken by human subjects, the dosage form of the present invention significantly suppresses the in-vivo release and the peak plasma levels of the drug that could arise from the ingestion of multiple pills are significantly suppressed.

The present inventors have further discovered useful abuse deterrent immediate release biphasic matrix solid dosage forms capable of deterring multiple modes of abuse including:

a. intentional abuse of overdosing or multiple unit administration by an addict or by a subject having suicidal intention, b. intentional abuse of extraction from multiple unit administration by an addict or by a subject having suicidal intention c. unintentional or accidental overdosing, d. concomitant alcohol consumption and resultant drug-alcohol interaction e. intentional abuse by nasal, parenteral, rectal or oral route f. separating two phases by physical means with an intention to abuse Particular embodiments have been discovered that simultaneously resolve two or three or all four of the above modes of abuse. Further embodiments of biphasic matrix solid dosage forms have been discovered that are resistant to physical means for separating the two phases with an intention to abuse.

BRIEF DESCRIPTION OF THE DRAWINGS

In the figures, the following notations apply:
101—Represents antacid;
102—Represents reverse enteric polymer;
103—Represents drug;
104—Represents intragranular phase;
105—Represents extragranular phase; and
106—Represents alcohol dose dumping resistance polymer.

FIG. 1 depicts an Abuse Deterrent. Immediate Release biphasic matrix solid dosage form of Biphasic matrix Type I having drug and reverse enteric polymer in intragranular phase and antacid such as alkalizer in the extragranular phase.

FIG. 2 depicts an Abuse Deterrent Immediate Release biphasic matrix Solid dosage form of Biphasic matrix Type II having drug, reverse enteric polymer and an alcohol dose-dumping resistance polymer in the intragranular phase and antacid such as alkalizer in the extragranular phase.

FIG. 3 depicts an Abuse Deterrent Immediate Release biphasic matrix solid dosage form of of Biphasic matrix Type III having a core containing drug and reverse enteric polymer and a coating of alcohol dose-dumping resistance polymer, the coated core forming an intragranular phase and antacid such as alkalizer in the extragranular phase.

Although not shown in FIGS. 1 to 11, additional properties in the above exemplary Types may be imparted, and particularly, for example where required, embodiments of the solid dosage form can be tamper or crush resistant or on crushing and other physical means the two phases cannot be separated.

Figure 12:
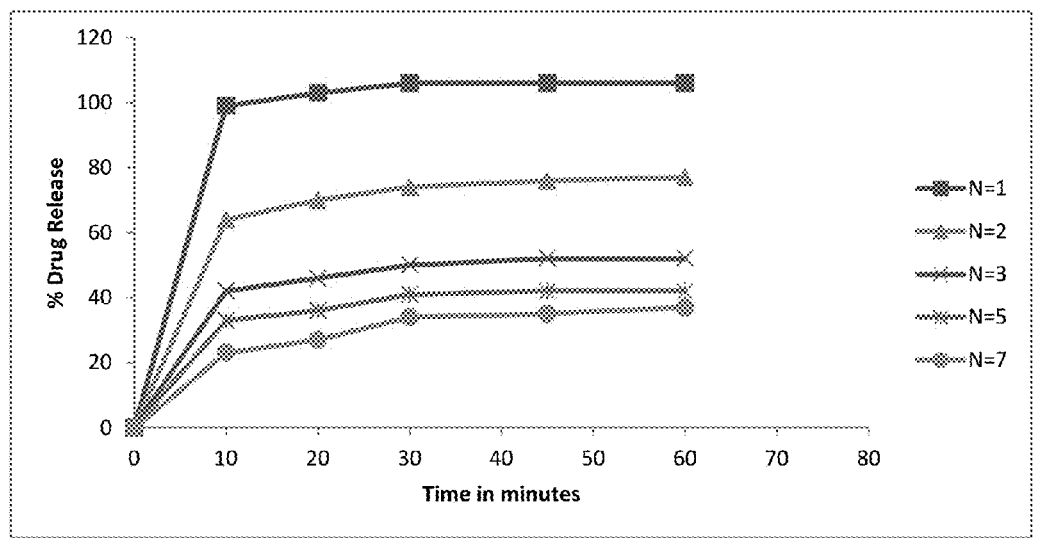

FIG. 12 is the graph of % release of the drug Vs time in minutes for the oral dosage form of Example 1, when N units of the dosage form are placed together in the dissolution bath to check the dissolution release of the drug.

Figure 13:
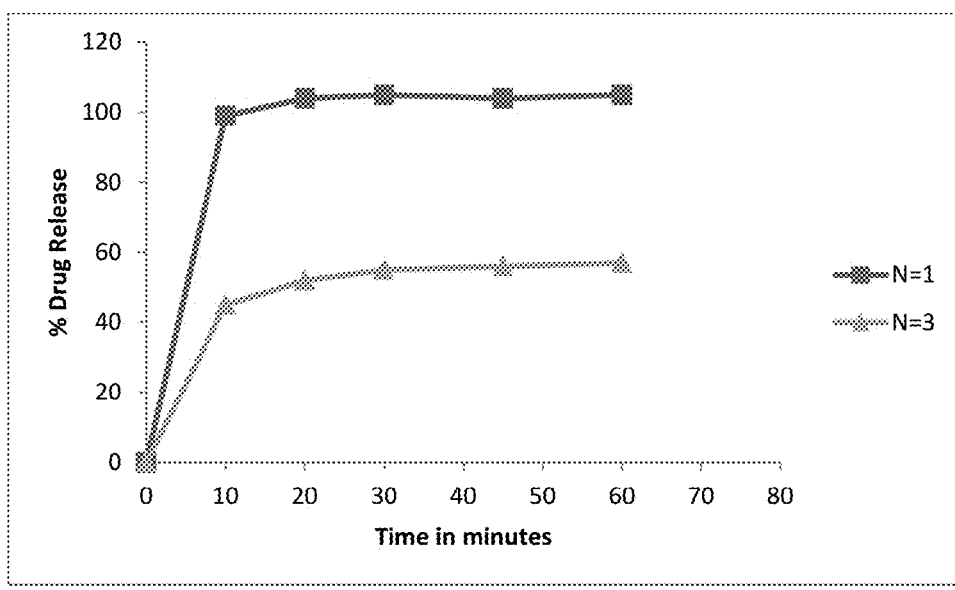

FIG. 13 is the graph of % release of the drug Vs time in minutes for the oral dosage form of Example 2, when N units of the dosage form are placed together in the dissolution bath to check the dissolution release of the drug.

Figure 14:
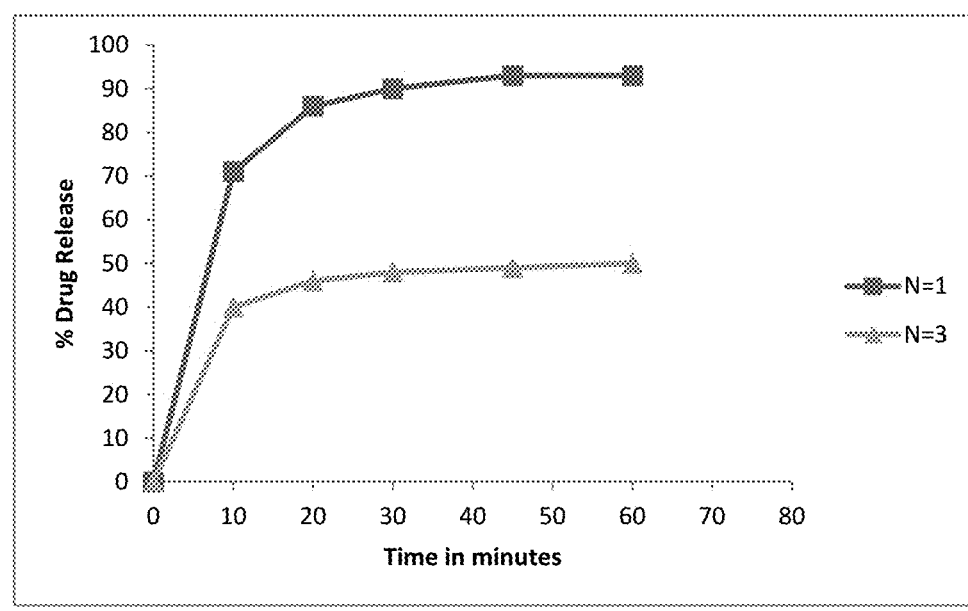

FIG. 14 is the graph of % release of the drug Vs time in minutes for the oral dosage form of Example 3, when N units of the dosage form are placed together in the dissolution bath to check the dissolution release of the drug.

Figure 15:
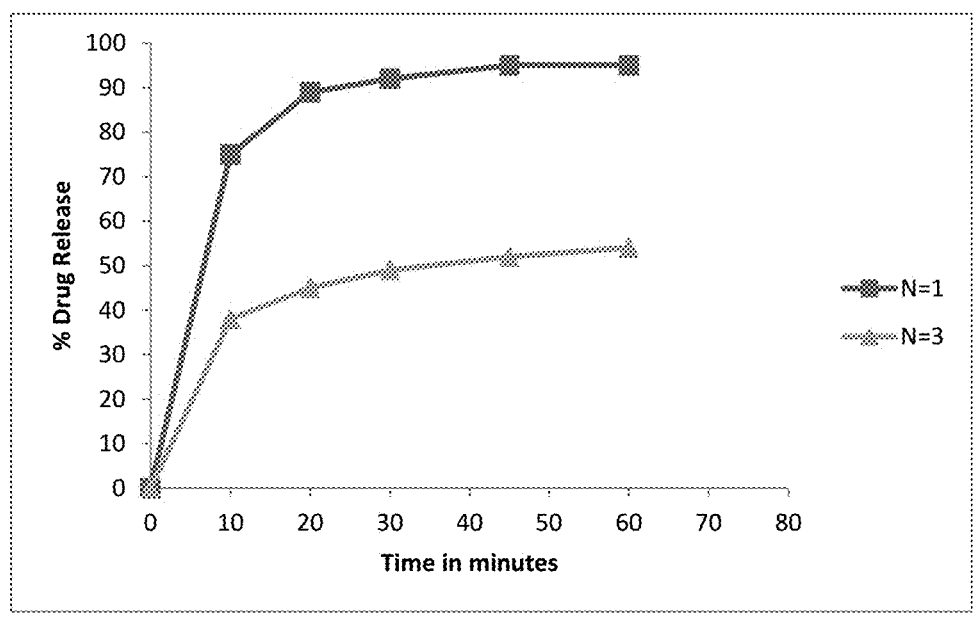

FIG. 15 is the graph of % release of the drug Vs time in minutes for the oral dosage form of Example 4, when N units of the dosage form are placed together in the dissolution bath to check the dissolution release of the drug.

Figure 16:
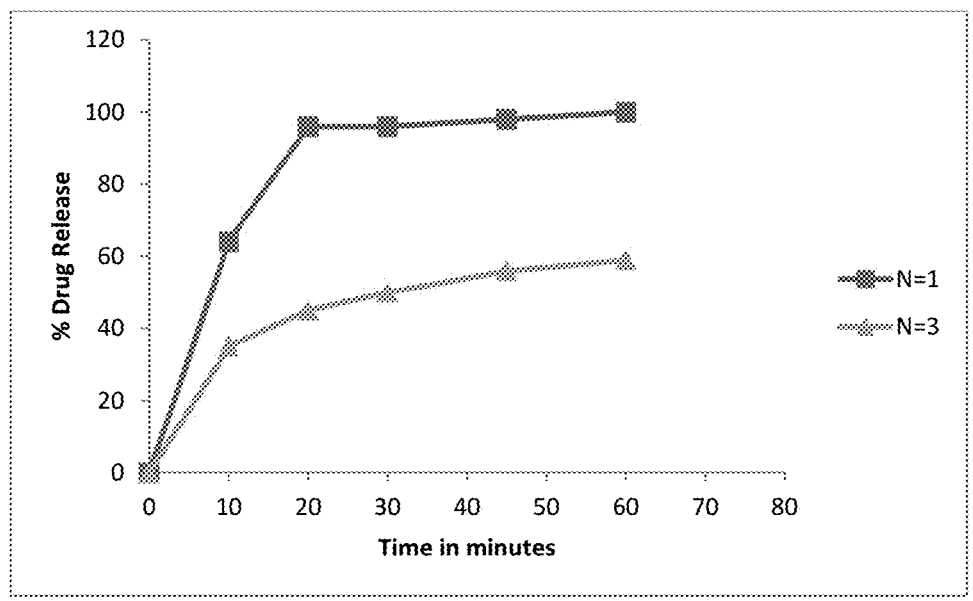

FIG. 16 is the graph of % release of the drug Vs time in minutes for the oral dosage form of Example 5, when N units of the dosage form are placed together in the dissolution bath to check the dissolution release of the drug.

Figure 17:
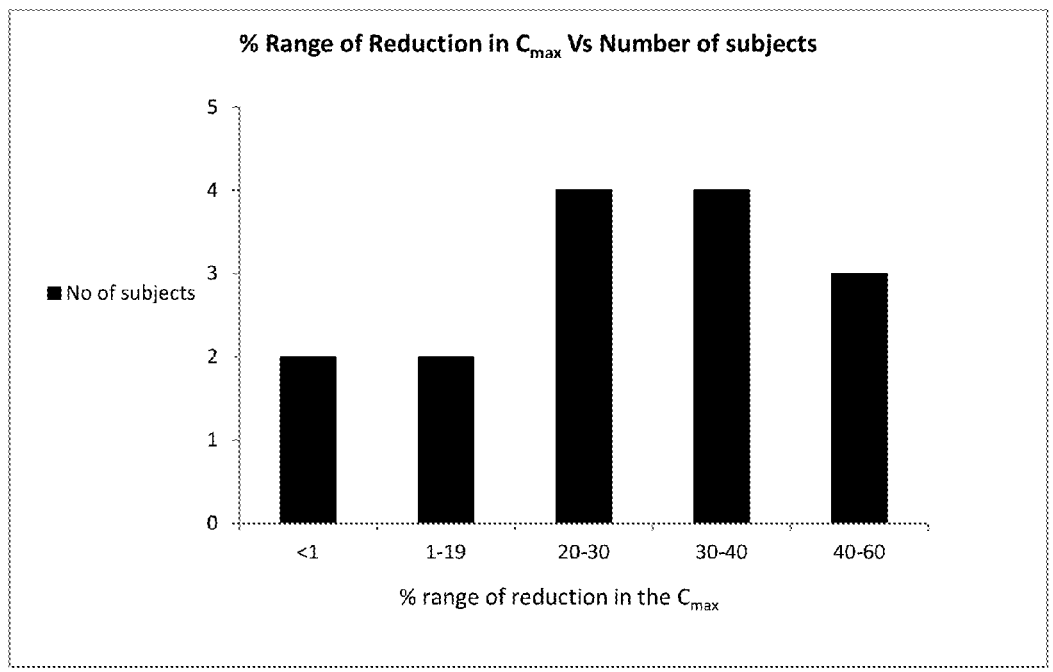

FIG. 17 is a graph of the % reduction in the peak plasma level range obtained by administration of more than the prescribed number of units of the dosage form (three) having a release inhibiting agent according to the present invention as compared to the peak plasma levels achieved by administration of the prescribed number of unit of the dosage form (one) that may or may not be devoid of any release inhibiting agent according to the present invention. FIG. 17 shows the graph of number of subjects falling in different % ranges of reduction in the $C_{max}$.

Figure 18:
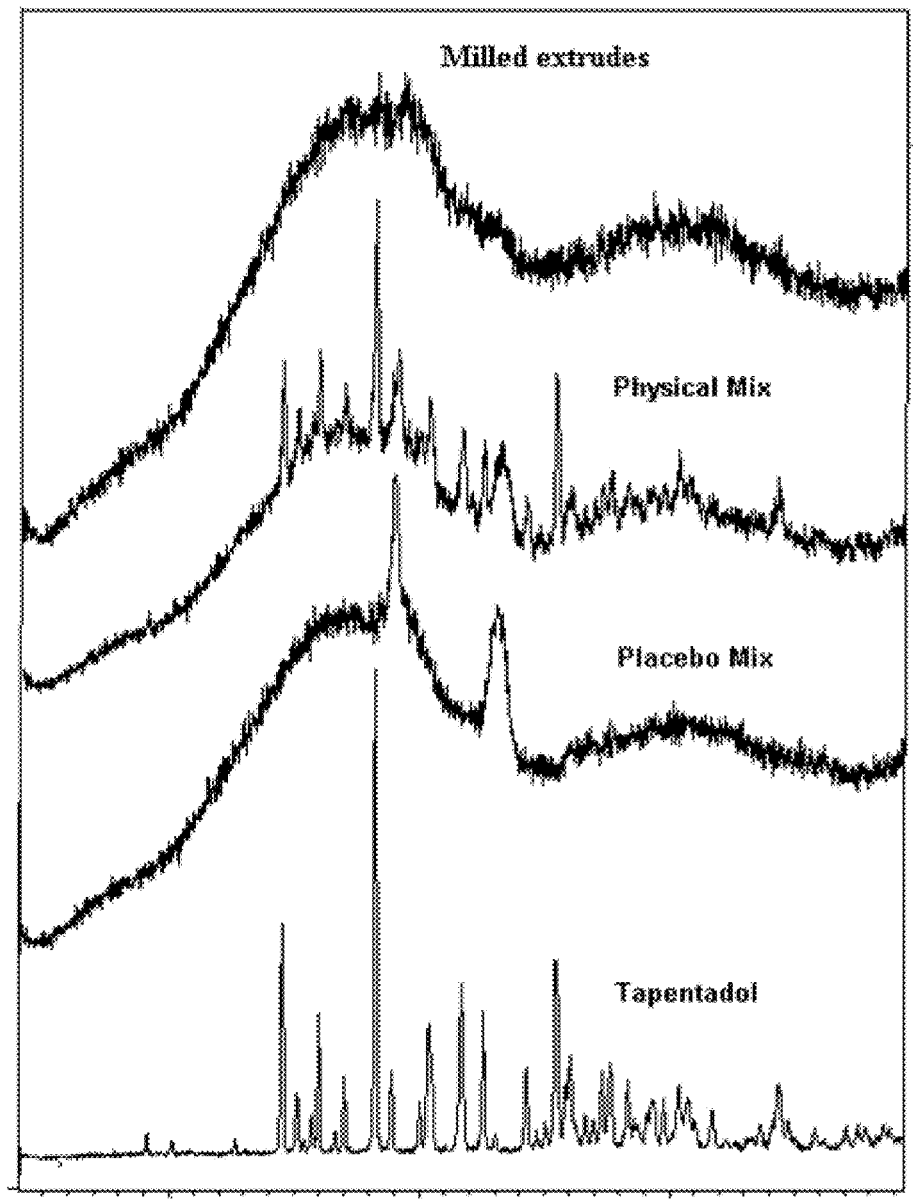

FIG. 18 provides a X-ray diffraction pattern of (i) model drug (Tapendadol), (ii) placebo mixture of reverse enteric polymer and alcohol dose-dumping resistance polymer, (iii) physical mixture of drug, reverse enteric polymer and alcohol dose-dumping resistance polymer and (iv) milled hot-melt extrudates of drug with reverse enteric polymer and alcohol dose-dumping resistance polymer.

DEFINITIONS

The term 'abuse' as used herein means the ingestion of the drugs by individuals with the intention of achieving a feel of high. The term 'abuse' also covers the over-ingestion of the drug intentionally or unintentionally. In case of intentional abuse it may be an attempt to suicide or driven by an addiction to the drug or in case of unintentional, it may be accidental consumption of more number of units of the drugs than the prescribed.

The phrase 'release inhibiting agent' used herein means agent that inhibits the release of the drug. According to the present invention, the release inhibiting agent is a combination of one or more reverse enteric polymers and an antacid.

The term, "reverse enteric polymer" as used herein refers to a polymer that is soluble in acidic solutions but is insoluble or alternatively swells or gels above a second higher pH value. Whether a polymer is insoluble above the second pH value is determined as follows:

500 mg of the reverse enteric polymer is dispersed in 100 ml of 0.05 N HCL and its pH adjusted to the second pH value by adding an alkali. Percent transmission of the dispersion is measured at 260 nm. The reverse enteric polymer is defined as 'insoluble' at and above the second specific pH value, if the percent transmission obtained at the second pH value is below 70%.

The term 'antacid' as used herein means any agent that suppresses the gastric acid environment. The antacid may work by physicochemical mechanisms that result in inhibition of in-vitro release as well as in-vivo release. For example, an alkalizer can increase the pH by neutralization of acid.

The term "granular" as used herein means an agglomerate of multiple particles bound together physically and encompassing granules, extrudates, pellets, pills, and the like.

The term Biphasic Matrix refers to the presence of atleast two distinct regions or phases, one an intragranular phase and the other an extragranular phase. The term 'intragranular phase' is meant to include granules or agglomerates or pellets, that are uncoated or are coated with an alcohol dose-dumping resistance polymer, the coating being considered as a part of the intragranular phase even though it is a coating. However, the coatings do not include coatings containing polymers that would be rate-controlling. For example, coating of reverse enteric polymer may be rate controlling at pH's above 5.5.

The term 'solid dispersion' as intended herein refers to a dispersion wherein the solid state of a drug in solid diluent as determined by X-ray diffractogram compared to a physical mixture of the drug and solid diluent made shows that the peaks characteristic of the crystalline drug are reduced or absent. Solid dispersions may also be called solid-state dispersions.

The term 'alcohol dose-dumping resistance polymer' refers to polymers that are generally soluble in water but are insoluble in 40% v/v solution in water used in an amount such that they allow immediate release of the drug in the absence of alcohol but provide improved resistance to alcohol dose-dumping as tested by dissolution in 40% v/v alcohol. Therefore, the term incorporates by definition, use of appropriate amounts.

DETAILED DESCRIPTION OF THE INVENTION

The abuse deterrent immediate release biphasic matrix solid dosage form of the present invention comprises a drug susceptible to abuse and a release inhibiting agent wherein the release inhibiting agent is a combination of one or more reverse enteric polymers and an antacid wherein atleast one polymer is a reverse enteric polymer. The second polymer may be an alcohol dose-dumping resistance polymer. The alcohol dose-dumping resistance polymer is used in amounts sufficient to prevent alcohol dose-dumping. Dose-dumping resistance of the solid dosage form is tested as illustrated in working Example 5A hereinbelow.

According to the present invention, the drug susceptible to abuse includes, but is not limited to, opioids, central nervous system (CNS) depressants and stimulants. The opioids are usually prescribed to treat pain. Central nervous system depressants are used to treat anxiety and sleep disorders and the stimulants are most often prescribed to treat attention deficit hyperactive disorder (ADHD). Opioids act by attaching to specific proteins called opioid receptors, which are found in the brain, spinal cord, gastrointestinal tract, and other organs in the body. When these drugs attach to their receptors, they reduce the perception of pain. Opioids can also produce drowsiness, mental confusion, nausea, constipation, and, depending upon the amount of drug taken, can depress respiration. Some people experience a euphoric response to opioid medications, since these drugs also affect the brain regions involved in reward. Those who abuse opioids may seek to intensify their experience.

According to the present invention, the drug susceptible to abuse may be an opioid. The opioids are selected from the group consisting of, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tapentadol, tilidine, tramadol, pharmaceutically acceptable salts thereof, and mixtures thereof.

According to the present invention, the drug susceptible to abuse may be central nervous system (CNS) depressants. The central nervous system (CNS) depressants are selected from the group consisting of, but are not limited to, alprazolam, bromazepam, chlordiazepoxied, clorazepate, diazepam, estazolam, flurazepam, halazepam, ketazolam, lorazepam, nitrazepam, oxazepam, prazepam, quazepam, temazepam, triazolam, methylphenidate, amobarbital, aprobarbotal, butabarbital, butalbital, methohexital, mephobarbital, metharbital, pentobarbital, phenobarbital, secobarbital, pharmaceutically acceptable salts thereof, and mixtures thereof. According to one embodiment of the present invention, the drugs that cause emergency situations when taken in overdose include, but are not limited to, opioids, central nervous system depressants and stimulants. The opioids are usually prescribed to treat pain. Central nervous system depressants are used to treat anxiety and sleep disorders and the stimulants are most often prescribed to treat attention deficit hyperactive disorder (ADHD). Opioids act by attaching to specific proteins called opioid receptors, which are found in the brain, spinal cord, gastrointestinal tract, and other organs in the body. When these drugs attach to their receptors, they reduce the perception of pain. Opioids can also produce drowsiness, mental confusion, nausea, constipation and depending upon the amount of drug taken, can depress respiration. Some people experience a euphoric response to opioid medications, since these drugs also affect the brain regions involved in reward. Those who abuse opioids may seek to intensify their experience.

Drugs suitable in the present invention include, but are not limited to, drugs whose overdose consumption, can lead to emergency visits, wherein the drugs is prescribed to be consumed by oral administration. The drugs may be selected from the group consisting of, but are not limited to cocaine, heroin, Cannabinoids, Marijuana, Synthetic cannabinoids Stimulants, 3,4-methylenedioxy-N-methylamphetamine (MDMA-Ecstasy), γ-hydroxybutyric acid (GHB), Flunitrazepam (Rohypnol), Ketamine, Lysergic acid diethylamide (LSD). It may be psychotherapeutic agents like antidepressants-monoamio oxidase inhibitors (MOA), phenylpiperazines like nefazodone and trazodone or selective serotonin norepinephrine reuptake Inhibitors (SSNRI) antidepressants like desvenlafaxine, duloxetine, venlafaxine. Other drugs include selective serotonin Reuptake Inhibitors (SSRI) antidepressants such as citalopram, fluoxetine, fluvoxamine, paroxetine and sertraline. Tetracyclic antidepressants (TCA) like maprotiline, mirtazapine, tricyclic antidepressants like amitriptyline, desipramine, doxepin, imipramine, nortriptyline are also suitable drugs according to the present invention. Atypical antipsychotics like bupropion, clozapine, olanzapine, quetiapine and risperidone, phenothiazine antipsychotics like chlorpromazine, fluphenazine, perphenazine, prochlorperazine, thioridazine, triflupromazine are also drugs that are suitable according to the present invention. Other class of drugs include, analgesics, antimigraine agents, cyclooxygenase inhibitors, Opiates, buprenorphine, codeine, dihydrocodeine, fenatyl, hydrocodone, hydromorphone, mepreidine, morphine, oxycodone, pentazocine, phenacetin, propoxyphene. Non-steroidal anti-inflammatory agents like ibuprofen, naproxen, salicylates, aspirin, acetaminophen, tramadol. Anorexiants like phenylpropanolamine. anticonvulsants like barbiturates anticonvulsants, benzodiazepine anticonvulsants, carbamate anticonvulsants, carbonic anhydrase inhibitor anticonvulsants, dibenzazepine anticonvulsants like carbamazepine, oxcarbazepine, rufinamide, fatty acid derivative anticonvulsants like divalproex, sodium valproic acid, gamma-aminobutyric acid analogs like gabapentin, hydantoin anticonvulsants like phenytoin, oxazolidinedione anticonvulsants, pyrrolidine anticonvulsants, succinimide anticonvulsants, triazine anticonvulsants. Antiemetic/antivertigo agents like 5HT3 receptor antagonists, anticholinergic antiemetics, phenothiazine antiemetics. antiparkinson agents like anticholinergic antiparkinson agents like benztropine, dopaminergic antiparkinsonism agents. Other drugs include barbiturates like phenobarbital, benzodiazepines like alprazolam, chlordiazepoxide, clonazepam, clorazepate, diazepam, flurazepam, lorazepam, oxazepam, temazepam, triazolam, misc. anxiolytics, sedatives, and hypnotics like buspirone chloral hydrate, diphenhydramine, doxylamine, hydroxyzine, zolpidem. CNS stimulants like amphetamine, dextroamphetamine, benzphetamine, dextroamphetamine, and methylphenidate. Other class of drugs includes skeletal muscle relaxants like carisoprodol, chlorzoxazone, cyclobenzaprine, metaxalone, methocarbamol tizanidine. cholinergic agonists, cholinesterase inhibitors, expectorants, selective phosphodiesterase-4 inhibitors, antiasthmatic, antitussives, leukotriene modifiers, mast cell stabilizers and mucolytics.

Categories of the drugs, that may be used in the present invention, further includes, centrally acting antiadrenergic agents like clonidine, beta-adrenergic blocking agents, beta blockers like atenolol, propranolol, calcium channel blocking agents, diuretics, carbonic anhydrase inhibitors, loop diuretics, potassium-sparing diuretics thiazide and thiazide-like diuretics, renin Inhibitors, vasopressin antagonists agents for hypertensive emergencies. Aldosterone receptor antagonists, angiotensin converting enzyme inhibitors, angiotensin II inhibitors and antiarrhythmic agents. It also includes drugs like anti-infectives like ameobicides, aminoglycosides, anthelmintics, antifungals like Azole antifungals and echinocandins, polyenes. Antimalarial agents like quinolones. Anti-tuberculosis agents like aminosalicylates, nicotinic acid derivatives, rifamycin derivatives, *streptomyces* derivatives. antiviral agents like adamantane antivirals, antiviral interferons, integrase strand transfer inhibitor, Neuraminidase inhibitors, non-nucleoside reverse-transcriptase inhibitors (NNRTIs), NRTIs, Protease inhibitors, Purine nucleosides. Antibiotics like carbapenems, cephalosporins, glycopeptide antibiotics glycylcyclines, lincomycin derivatives, macrolide derivatives, ketolides, macrolides, penicillins, aminopenicillins, antipseudomonal penicillins, Beta-lactamase inhibitors, Natural penicillins penicillinase resistant penicillins, quinolones, sulfonamides, tetracyclines, and urinary anti-infective. antineoplastics like alkylating agents, Anti-CTLA-4 monoclonal antibodies, antimetabolites antineoplastic antibiotics, antineoplastic hormones, antineoplastic interferons, CD20 monoclonal antibodies, EGFR inhibitors, HER2 inhibitors, histone deacetylase inhibitors, mitotic inhibitors, mTOR inhibitors, VEGF/VEGFR inhibitors. It also includes drugs like coagulation modifiers like anticoagulants, coumarins and indanediones, Factor Xa inhibitors, Heparins, Thrombin inhibitors, Anti-platelet agents, Glycoprotein platelet inhibitors, Platelet aggregation inhibitors, Heparin antagonists, Platelet-stimulating agents, thrombolytics. Gastrointestinal agents like 5-aminosalicylates, Antacids, Anti-diarrheal, digestive enzymes, functional bowel disorder agents, chloride channel activators, peripheral opioid receptor antagonists, Serotonin-ergic neuroenteric modulators, Gallstone solubilizing agents, GI stimulants, *H. pylori* eradication agents, H2 antagonists Laxatives, Proton pump inhibitors. Genitourinary tract agents, Impotence agents, Tocolytic agents, Urinary antispasmodics, Urinary pH modifiers, uterotonic agents. Hormones like 5-Alpha-reductase inhibitors, adrenal cortical steroids like corticotropin, glucocorticoids, mineralocorticoids, adrenal corticosteroid inhibitors, antidiuretic hormones, anti-gonadotropic agents, anti-thyroid agents, calcitonin, gonadotropin-releasing hormone antagonists, growth hormone receptor blockers, growth hormones, insulin-like growth factor, parathyroid hormone and analogs, progesterone receptor modulators, prolactin inhibitors, selective estrogen receptor modulators, sex hormones androgens and anabolic steroids, contraceptives, Estrogens, gonadotropin-releasing hormone and analogs gonadotropins, progestins, sex hormone combinations, somatostatin and somatostatin analogs, synthetic ovulation stimulants, thyroid hormones. Immunologic agents like immune globulins, immunostimulants, Bacterial vaccines, colony stimulating factors. interferons, immunosuppressive agents, calcineurin inhibitors, Interleukin inhibitors, Selective immunosuppressants, TNF alfa inhibitors metabolic agents like antidiabetic agents, Alpha-glucosidase inhibitors, Amylin analogs, Antidiabetic combinations like Dipeptidyl peptidase 4 inhibitors, Insulin, meglitinides, biguanides, sulfonylureas, thiazolidinediones, antigout agents, antihyperlipidemic agents, antihyperlipidemic combinations. Other classes of drugs further include bile acid sequestrants, cholesterol absorption inhibitors, Fibric acid derivatives, HMG-CoA reductase inhibitors, antihyperuricemic agents, bone resorption inhibitors, bisphosphonates, glucose elevating Agents, lysosomal enzymes, Peripherally acting antiobesity agents and miscellaneous metabolic agents. Antipsoriatics, Antirheumatics, chelating agents, cholinergic muscle stimulants, psoralens, smoking cessation agents. radiologic agents like radio-contrast agents, and radiopharmaceuticals According to the present invention, the drugs that cause emergency situations when taken in overdose may be central nervous system depressants. The central nervous system depressants are selected from the group consisting of, but are not limited to, alprazolam, bromazepam, chlordiazepoxied, clorazepate, diazepam, estazolam, flurazepam, halazepam, ketazolam, lorazepam, nitrazepam, oxazepam, prazepam, quazepam, temazepam, triazolam, methylphenidate, amobarbital, aprobarbotal, butabarbital, butalbital, methohexital, mephobarbital, metharbital, pentobarbital, phenobarbital, secobarbital.

According to the present invention, the drug susceptible to abuse may be central nervous system (CNS) stimulants. The central nervous system (CNS) stimulants are selected from the group consisting of, but are not limited to, amphetamines, dextroamphetamine, methamphetamine, methylphenidate, pharmaceutically acceptable salts thereof and mixtures thereof.

The "reverse enteric polymer" used in the solid dosage form of the present invention is a polymer that is soluble in acidic solutions but is insoluble or alternatively swells or gels above a second higher pH value. In several of the embodiments, as herein described, the reverse enteric polymer functions as a release rate controlling polymer above a critical pH but has little rate controlling ability below the critical pH. Examples are found in polymers that have group capable of accepting the hydrogen ion from an acid below the critical pH and thus becoming soluble in acid environment and fall under the class of pH dependent polymers.

The reverse enteric polymer used is selected from polymers that are prepared by polymerizing a mixture of the hydrophobic and basic monomer or a mixture of the hydrophobic, hydrophilic and basic monomer wherein the basic monomer may be selected from the group consisting of dimethyl amino ethyl acrylate, diethyl amino ethyl ethacrylate, diethyl amino ethyl acrylate, piperidine ethyl methacrylate and 2-tert-butyl amino ethyl methacrylate.

An example of a preferred reverse enteric polymer i.e. a pH dependent polymer used is a methyl methacrylate butyl methacrylate-dimethyl aminoethyl methacrylate copolymer which is a cationic copolymer synthesized from dimethyl aminoethyl methacrylate and neutral methacrylic acid esters, more particularly as is commercially available under the trade name Eudragit™ E which is soluble below an acidic pH such as pH 5 and swellable and permeable above about a higher pH such as above 5.0. It is depicted by the following structure.

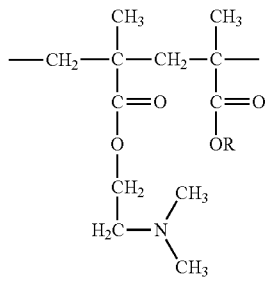

R = CH₃, C₄H₉

The repeating unit in the polymer has the following structure: where R represents CH3 and C₄H₉ groups and the polymer has a molecular weight about 1,50,000. They may exist in different physical forms. The Eudragit™ E 100 product is granular, the Eudragit™ E 12.5 product is a 12.5% solution of E 100 in isopropanol and acetone, and the Eudragit EPO product is a fine powder made from E 100. Various grades of this polymer are commercially available from Evonik, Germany. The amount of Eudragit™ E in the present invention varies from 0.5% to about 30% by weight of the composition, preferably about 2% to about 30% by weight of the composition, more preferably about 5% to about 20% by weight of the composition. The ratio of weight of polymer to the weight of drug varies from 0.5 to about 8.0, preferably about 3.0 to about 8.0, more preferably about 6.8. The amount of this reverse enteric polymer may be expressed in terms of its weight ratio. The embodiments, having biphasic matrix type i.e when the reverse enteric polymer is in admixture with the drug, the weight ratio of the methyl methacrylate butyl methacrylate-dimethyl aminoethyl methacrylate copolymer to the drug susceptible to abuse, such as tapendalol hydrochloride, a highly water soluble drug, can vary from 4 to 15, preferably about 8. However, the ratio of methyl methacrylate butyl methacrylate-dimethyl aminoethyl methacrylate copolymer to the drug susceptible to abuse may vary depending upon the solubility and the dose of the drug, present in each unit.

Other suitable examples of such pH dependent polymers may be found in the art. It is beneficial to use polymers which are soluble only at pH 5.5 or below, that are additionally also impermeable since this further helps control the dissolution rate. In more preferred embodiments of the present invention the reverse enteric polymer is selected from a polymer that is soluble below about pH 5 but insoluble above about pH 5.5. For example, US20050137372 disclosed similar polymers prepared by polymerizing a mixture of the hydrophobic and basic monomer or a mixture of the hydrophobic, hydrophilic and basic monomer wherein the basic monomer may be selected from the group consisting of dimethyl amino ethyl acrylate, diethyl amino ethyl ethacrylate, diethyl amino ethyl acrylate, piperidine ethyl methacrylate and 2-tert-butyl amino ethyl methacrylate. Several other polymers having basic functional groups and thus the desired pH dependent solubility behavior can be used according to the present invention. Poly(lysine) (PL), poly(ethylenimine) (PEI) and chitosan are examples of such polymers.

The reverse enteric polymer used in the compositions of the present invention may be used in the form of a dispersion or in a powder form for preparing the compositions.

It is thus within skill in the art to use existing polymers with the appropriate basic ionizable groups or to synthesize new such polymers by incorporating monomers having basic ionizable groups and any such polymer may be used according to the scope of the present invention.

Suitable examples of the reverse enteric polymer that is soluble at an acidic but is insoluble at a second higher pH value, include, but are not limited to, methyl methacrylate and diethylaminoethyl methacrylate and the like. Any other reverse enteric polymer having such properties is encompassed within the scope of this embodiment of the present invention. In one specific preferred embodiment, the reverse enteric polymer that can be utilized in the present invention is a copolymer comprising amino and/or alkylamino and/or dialkyl amino groups such as copolymers comprising methyl methacrylate and diethylaminoethyl methacrylate such as commercially available as Kollicoat® Smartseal 30 D from BASF. The polymer has a molecular weight of about 200,000 and a glass transition temperature of 57 to 63° C. The embodiments, having biphasic matrix type i.e when the reverse enteric polymer is in admixture with the drug, the ratio of methyl methacrylate and diethylaminoethyl methacrylate to the drug susceptible to abuse, such as tapendalol hydrochloride, a highly water soluble drug, can vary from 6 to 50, preferably about 5 to 15.

Thus, in one aspect of abuse deterrent immediate release biphasic matrix solid dosage form of the present invention comprises a drug susceptible to abuse and a release inhibiting agent wherein the release inhibiting agent is a combination of polymer and an antacid wherein the antacid is an alkalizer and further wherein atleast one polymer is a reverse enteric polymer and functions as a release rate controlling polymer above a specific pH but has little rate controlling ability below the critical pH. Alternatively, the antacid may be a substance that suppresses gastric acid secretion for example, H2-antagonist.

The term "alkalizer" as used herein refers to physiologically acceptable substances that neutralize acid. Examples of alkalizer include, but are not limited to calcium carbonate, disodium hydrogen phosphate, trisodium orthophosphate, sodium hydroxide, sodium carbonate, potassium hydroxide, sodium bicarbonate, dipotassium carbonate, tromethamine, aluminum trihydroxide, magnesium dihydroxide, aluminium oxide, magnesium oxide and mixture thereof. The amount of alkalizer used in a single unit is selected so that it will not be sufficient to raise the stomach pH to above a critical pH for example 5 or neutral pH; but when more than the prescribed number of units are administered, it is sufficient to raise the pH of the stomach to above the critical pH. Usually the amount of alkalizer in when more than the prescribed number of units should atleast raise the pH of 500 ml of 0.01 N HCl to above the critical pH, preferably the amount should be greater and raise the pH of 1000 ml of 0.01N HCl to above the critical pH, and more preferably it may exceed that amount sufficiently to neutralize any immediate rebound secretion of acidic gastric fluids in response to the alkalizer. The amount of alkalizer in one single unit is however selected so that it does not raise the pH of 500 ml, preferably 1000 ml of 0.01N HCl to above the critical pH so that when a single unit is orally administered the polymer does not behave like a rate controlling polymer but when more than the prescribed number of units are administered, it behaves like a rate controlling polymer and inhibits release.

Various embodiments according to the present invention are categorized into various types. These will be explained in great details hereinafter.

The solid dosage form of the present invention may include a second polymer which is an alcohol dose-dumping resistance polymer. These polymers may be soluble or insoluble in 100% water but are insoluble in 40% v/v solution of alcohol in water. These polymers may be incorporated either in intragranular phase or extragranular phase and when used in sufficient amount provide improved resistance to alcohol dose dumping and at the same time they do not slow down the rate of release of the drug allowing the dosage form to perform as an immediate release dosage form. Examples of such polymers include, but are not limited to, ethyl cellulose, polyvinyl alcohol, polyethylene oxide, sodium starch glycolate and the like and mixture thereof. The polymers that do not affect or control the release of the drug from the immediate release dosage form are suitable to be incorporated into the abuse deterrent immediate release solid dosage form according to the present invention.

The solid dosage form of the present invention may be fabricated into a suitable form such as sachets, capsules or tablet by methods known in the art and using conventional excipients known in the art such as diluents or fillers, binders, disintegrants, stabilisers glidants, lubricants, surfactants, solubilizing agents, preservatives, coloring agents and others as may be necessitated by the drug to be incorporated in the dosage form. In one specific embodiment, the inventors found that certain disintegrants exhibit reduced swelling power in alcoholic solutions but show very good swelling and disintegration effect in aqueous medium that are devoid of alcohol. Such type of disintegrants is preferable. These type of disintegrants, not only provide resistance to tampering by extracting with alcohol, but help in avoiding dose dumping when the solid dosage form is ingested with alcohol or alcoholic beverages. Examples of such disintegrants include, but are not limited to, sodium starch glycolate, polacrillin potassium and the like and mixtures thereof.

Biphasic matrix solid dosage form refers to solid dosage forms having an intragranular phase and an extragranular phase. Intragranular phase is formed by agglomeration of particles into granules, extrudates, pellets, mini-tablets or tablets etc.

The biphasic matrix solid dosage forms may be further sub categorized into different types referred to as Type I, Type II, Type III, Type IV, Type V, Type VI, Type VII, Type VIII, Type IX, Type X, Type XI and Type XII. Each of these types is illustrated by way of FIGS. 1 to 12.

Type I as depicted in FIG. 1 refers to an Abuse Deterrent Immediate Release Solid dosage form of Biphasic matrix Type I having drug and reverse enteric polymer in intragranular phase and antacid such as alkalizer in the extragranular phase.

Type II depicted in FIG. 2 refers to an Abuse Deterrent Immediate Release Solid dosage form of Biphasic matrix Type II having drug, reverse enteric polymer and an alcohol dose-dumping resistance polymer in the intragranular phase and antacid such as alkalizer in the extragranular phase.

Type III depicted in FIG. 3 refers to an Abuse Deterrent Immediate Release Solid dosage form of Biphasic matrix Type III having a core containing drug and reverse enteric polymer and a coating of alcohol dose-dumping resistance polymer, the coated core forming an intragranular phase and antacid such as alkalizer in the extragranular phase.

Figure 4:
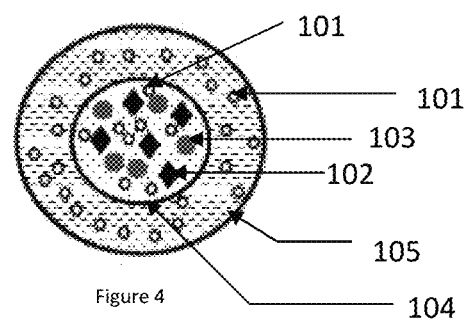
FIG. 4 depicts an Abuse Deterrent Immediate Release biphasic matrix solid dosage form of Biphasic matrix Type IV with drug, reverse enteric polymer and a part of the antacid such as alkalizer in intragranular phase and part of the antacid such as alkalizer, in the extragranular phase.

Type IV depicted in FIG. 4 refers to an Abuse Deterrent Immediate Release Solid dosage form of Biphasic matrix Type IV with drug, reverse enteric polymer and a part of the antacid such as alkalizer in intragranular phase and part of the antacid such as alkalizer, in the extragranular phase.

Figure 5:
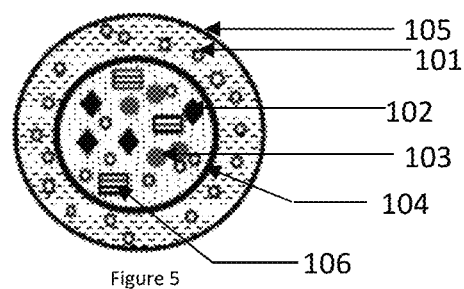
FIG. 5 depicts an Abuse Deterrent Immediate Release biphasic matrix solid dosage form of Biphasic matrix Type V with intragranular phase containing drug, a part of the antacid such as alkalizer, reverse enteric polymer and an alcohol dose-dumping resistance polymer and a part of the antacid such as alkalizer, in the extragranular phase.

Type V depicted in FIG. 5 refers to an Abuse Deterrent Immediate Release Solid dosage form of Biphasic matrix Type V with drug, reverse enteric polymer, a part of the antacid such as alkalizer and an alcohol dose-dumping resistance polymer in intragranular phase and part of the antacid such as alkalizer, in the extragranular phase.

Figure 6:
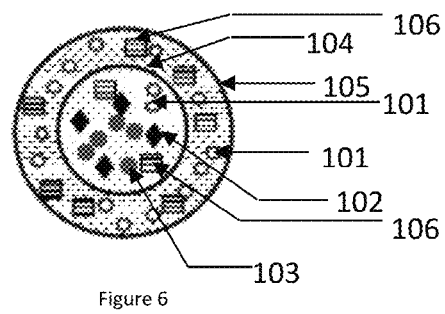
FIG. 6 depicts an Abuse Deterrent Immediate Release biphasic matrix solid dosage form of Biphasic Matrix Type VI with drug, reverse enteric polymer and a part of the alkalizer and an alcohol dose-dumping resistance polymer in intragranular phase and part of the antacid such as alkalizer and an alcohol dose-dumping resistance polymer, in the extragranular phase.

Type VI depicted in FIG. 6 refers an Abuse Deterrent Immediate Release Solid dosage form of Biphasic matrix Type VI with intragranular phase containing drug, reverse enteric polymer, an alcohol dose-dumping resistance polymer and an extragranular phase containing an antacid such as alkalizer and an alcohol dose-dumping resistance polymer.

Figure 7:
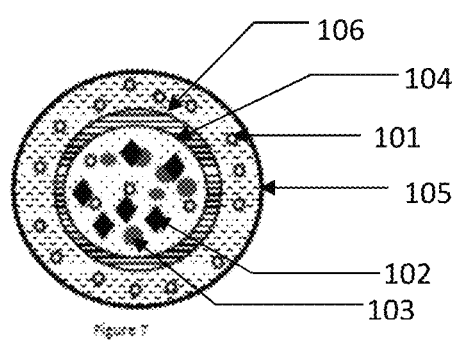
FIG. 7 depicts an Abuse Deterrent Immediate Release biphasic matrix solid dosage form of Biphasic matrix Type VII, having a core containing a drug, reverse enteric polymer, a part of the antacid such as alkalizer and a coat containing alcohol dose-dumping resistance polymer, the coated core forming an intragranular phase and a part of the antacid such as alkalizer in the extragranular phase.

Type VII depicted in FIG. 7 refers to an Abuse Deterrent Immediate Release Solid dosage form of Biphasic matrix Type VII having a core containing a drug, reverse enteric polymer, a part of the antacid such as alkalizer and a coat containing alcohol dose-dumping resistance polymer, the coated core forming an intragranular phase and a part of the antacid such as alkalizer in the extragranular phase.

Figure 8:
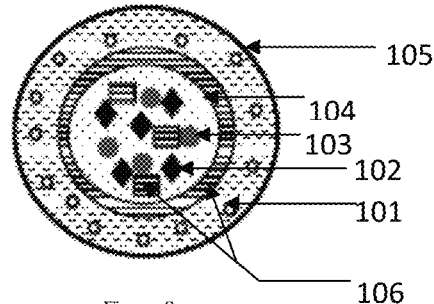
FIG. 8 depicts an Abuse deterrent Immediate release biphasic matrix solid dosage form of Biphasic matrix Type VIII having a core containing drug, reverse enteric polymer and a part of the alcohol dose-dumping resistance polymer; the core being coated with remaining part of the alcohol dose-dumping resistance polymer, the coated core forming an intragranular phase and an extragranular phase having an antacid such as alkalizer.

Type VIII depicted in FIG. 8 refers to an Abuse Deterrent Immediate Release Solid dosage form of Biphasic matrix Type VIII having a core containing drug, reverse enteric polymer and a part of alcohol dose-dumping resistance polymer; the core being coated with remaining part of the alcohol dose-dumping resistance polymer, the coated core forming an intragranular phase and an extragranular phase having an antacid such as alkalizer.

Figure 9:
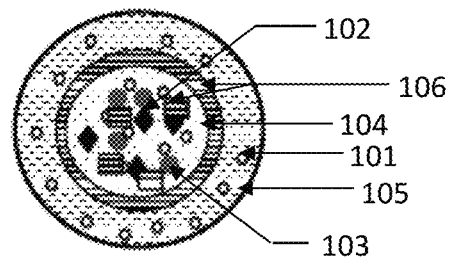
FIG. 9 depicts an Abuse Deterrent Immediate Release biphasic matrix solid dosage form of Biphasic matrix Type IX having a core containing drug, reverse enteric polymer, a part of the antacid such as alkalizer and an alcohol dose-dumping resistance polymer, wherein the core is coated with alcohol dose-dumping resistance polymer, the coated core forming the intragranular phase and an extragranular phase containing a part of the antacid such as alkalizer.

Type IX depicted in FIG. 9 refers to an Abuse Deterrent Immediate Release Solid dosage form of Biphasic matrix Type IX having a core containing drug, reverse enteric polymer, a part of the antacid such as alkalizer and an alcohol dose-dumping resistance polymer, wherein the core is coated with alcohol dose-dumping resistance polymer, the coated core forming the intragranular phase and an extragranular phase containing a part of the antacid such as alkalizer.

Figure 10:
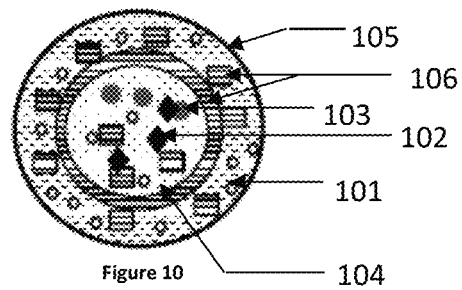
FIG. 10 depicts an Abuse Deterrent Immediate Release biphasic matrix Solid dosage form of Biphasic matrix Type X having a core containing drug, reverse enteric polymer, part of the antacid such as alkalizer and a part of an alcohol dose-dumping resistance polymer, the core is coated with a part of the alcohol dose-dumping resistance polymer, the coated core forming an intragranular phase and remaining part of the alcohol dose-dumping resistance polymer and a part of the antacid such as alkalizer in the extragranular phase.

Type X depicted in FIG. 10 refers to an Abuse Deterrent Immediate Release Solid dosage form of Biphasic matrix Type X having a core containing drug, reverse enteric polymer, part of the antacid such as alkalizer and a part of the alcohol dose-dumping resistance polymer, the core is coated with a part of the alcohol dose-dumping resistance polymer, the coated core forming an intragranular phase and remaining part of the alcohol dose-dumping resistance polymer and a part of the antacid such as alkalizer in the extragranular phase.

Figure 11:
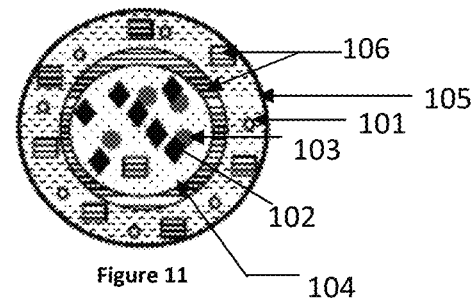
FIG. 11 depicts an Abuse Deterrent Immediate Release biphasic matrix solid dosage form of Biphasic matrix Type XI having a core containing drug, reverse enteric polymer and an alcohol dose-dumping resistance polymer, which is coated with alcohol dose-dumping resistance polymer, forming an intragranular phase and an antacid such as alkalizer and a part of the alcohol dose-dumping resistance polymer forming an extragranular phase.

Type XI depicted in FIG. 11 refers to an Abuse Deterrent Immediate Release Solid dosage form of Biphasic matrix Type XI having a core containing drug, reverse enteric polymer and an alcohol dose-dumping resistance polymer, which is coated with alcohol dose-dumping resistance polymer, forming an intragranular phase and an antacid such as alkalizer and a part of the alcohol dose-dumping resistance polymer forming an extragranular phase.

In certain embodiments of the abuse deterrent immediate release dosage form comprises a drug susceptible to abuse and a release inhibiting agent, the release inhibiting agent consisting of a combination of atleast two polymers and an antacid wherein atleast one first polymer is a reverse enteric polymer and atleast one second polymer is an alcohol dose-dumping resistance polymer wherein the reverse enteric polymer, alcohol dose-dumping resistance polymer and the antacid are present in amounts such that when more than the prescribed number of units, such as two or more number of units, of the dosage form are tested for in-vitro dissolution in 500 ml of an acidic medium such as for example, 0.01N HCl, by USP dissolution method, the release is inhibited as compared to the immediate release of the prescribed number of units, such as, for example, atleast 80±5% of drug in a single prescribed unit of the dosage form in one hour. In one example, 0.01 HCL with 40% ethanol by volume was used as a dissolution medium. The in vitro dissolution was conducted in Type II, USP apparatus, rotating at a speed of 50 rpm. Certain embodiments may also have a polymer incorporated in a manner to provide tamper resistance.

The reverse enteric polymer and the antacid together function as the release inhibiting agent. The amount and the ratios of the reverse enteric polymer to the antacid depend on the type of matrix and the ratio can vary from 1:1 to 1:10. The amounts and ratios can be determined as exemplified in the examples and amounts that function to allow immediate release when only one single unit of the dosage form are used but function as release inhibiting agent when multiple units are used may be determined and may vary depending on the Type of solid dosage form involved and the choice of the reverse enteric polymer and the antacid. In embodiment of the Biphasic matrix type where the reverse enteric polymer is only present in the intragranular phase and the antacid only in the extragranular phase, the ratio of the reverse enteric polymer and drug is about 7 and the amount of antacid ranges from about 25% of the total dosage form. It may be noted that amount of the antacid as well as its ionization capacity determines how much the release can be inhibited from the more than the prescribed number of units, for instance, in this case, it was found that when a combination of sodium bicarbonate and magnesium oxide were used, about 25% by weight was found not to inhibit the release from 2 units, but when more than 2 units were subjected to dissolution, the release was inhibited. In the cases where the antacid is a combination of sodium bicarbonate and magnesium oxide, at a concentration of about 30% by weight, the solid dosage form was found to provide inhibition when two units were tested. In this case, therefore, the immediate release solid dosage form can be designed to incorporate the unit dose of the drug, in a single unit. This shows that the immediate release dosage form of the present invention can be altered as per the need of the number of units at which inhibition is desired.

In one particular embodiment, the intragranular phase is prepared by wet granulation. These granules are mixed with the extragranular ingredients and can be converted into a tablet by compression or the phases may be mixed and filled into hard gelatin.

In one particular embodiment, the reverse enteric polymer is present in admixture with the drug in an internal phase and the antacid is present in an external phase.

According to one aspect, the present invention provides an abuse deterrent immediate release biphasic matrix solid dosage form comprising: a drug susceptible to abuse and a release inhibiting agent, the release inhibiting agent consisting of a combination of atleast two polymers and an antacid wherein atleast one first polymer is a reverse enteric polymer and atleast one second polymer is alcohol dose-dumping resistance polymer, wherein the reverse enteric polymer and the antacid such as alkalizer are present in amounts such that when more than the prescribed number of units of the dosage form are tested for in-vitro dissolution in 500 ml, of an acidic medium by USP dissolution method, the release is inhibited as compared to the immediate release of drug from a single or prescribed number of units in 2 hours when a single or prescribed number of units, of the dosage form is tested. The amount of reverse enteric polymer present in the current embodiment is from about 14 to 75%. The amount of antacid present extragranularly ranges from about 47 to 68%. The alcohol dose-dumping resistance polymer present intragranularly can vary from about 2 to 15%. The granules of the present embodiment are made by hot melt extrusion technique.

In another embodiment, the reverse enteric polymer, the alcohol dose-dumping resistance polymer and antacid are present in admixture with the drug in the intragranular phase. The antacid component in the present embodiment is also present in the extragranular phase.

In this embodiment, the amount of reverse enteric polymer can vary from about 5% to about 15%, the amount of alcohol dose-dumping resistance polymer can vary from about 0.5% to 5%, preferably, about 2.5%. In this embodiment the reverse enteric polymer is present in a range of about 19 to 67% of the intragranular phase. The alcohol dose-dumping resistance polymer is present in a range of about 4 to 14% of the intragranular phase. The antacid present intragranularly is in a range of about 1 to 9% and the antacid present extragranularly is in a range of about 50% to 55% by weight. The granules of the present embodiment are made by the hot melt extrusion technique.

According to one specific embodiment, the abuse deterrent immediate release solid dosage form is resistant to alcohol. That is, the dosage form does not increase the release rate when concomitantly administered with alcohol or alcoholic beverages and preferably, provides reduced rate of release in alcoholic medium as compared to non-alcoholic medium, when tested using standard in vitro dissolution testing methods. In one embodiment dosage form comprises a drug susceptible to abuse and a release inhibiting agent, the release inhibiting agent consisting of a combination of atleast two polymers and an antacid present intragranularly wherein atleast one first polymer is a reverse enteric polymer and atleast one second polymer is alcohol dose-dumping resistance polymer. In this embodiment the alcohol dose-dumping resistance polymer and antacid are also present extragranularly. The range of alcohol isoluble polymer present intragranularly ranges from about 4 to 5% and the alcohol dose-dumping resistance polymer present extragranularly ranges from about 12 to 16%. The reverse enteric polymer present in this embodiment ranges from about 19 to 20%. The antacid present intragranularly ranges from about 2 to 3% and the antacid present extragranularly ranges from about 32 to 49%. The granules of the present embodiment are prepared by hot melt extrusion and spheronization technique.

In another embodiment the dosage form comprises of a matrix of the drug in contact with a release inhibiting agent and an antacid present only as an intragranular phase. The release inhibiting agent consisits of a combination of atleast one first polymer which is a reverse enteric polymer and an alcohol dose-dumping resistance polymer. In these embodiments, the reverse enteric polymer is present in a range of about 29 to 30% and the antacid is present in the range of about 2 to 5%. The alcohol dose-dumping resistance polymer of the same embodiment can vary in amounts in the range of 7 to 8%. The granules of the present embodiment are prepared by the hot melt extrusion technique.

It was found that incorporation of the antacid in the intragranular phase and the extragranular phase provided various advantages such as below:

1. The amount of antacid in the extragranular phase that is required to provide the multiple pill abuse resistance was considerably lower when compared with the solid dosage form that is devoid of an antacid in the intragranular phase, but present in the extragranular phase.

2. The solid dosage form according to these embodiment of Type V, VI, VII, VIII, X, XI, were found to be resistant to abuse by nasal route and tampering by various mediums used by abuser such as acidic and alcoholic beverages and the like, as compared to embodiments of Type, I, II, III, IV, IX, According to another aspect, the present invention provides an abuse deterrent immediate release biphasic matrix solid dosage form comprising:
 a drug susceptible to abuse and a release inhibiting agent,
 the release inhibiting agent consisting of a combination of
  at least two polymers and an antacid wherein at least one first polymer is a reverse enteric polymer, and at least an alcohol dose-dumping resistance polymer,
 wherein the reverse enteric polymer and the antacid are present in amounts such that when more than two units of the dosage form are tested for in-vitro dissolution in 500 ml, of 0.01N HCl, Type II USP apparatus (Paddle) rotating at a speed of 50 rpm, the release is inhibited as compared to the immediate release of drug from a single units in 2 hours when a single unit of the dosage form is tested.

In certain embodiments of the present invention, the internal (intragranular) phase is prepared via hot melt extrusion. When the antacid is present in the external phase and the drug is in admixture with the reverse enteric polymer to form an internal phase, then the amount of antacid can vary from about 15 to 60%, preferably, 25 to 50% by weight of the solid dosage form. In certain embodiments, the internal phase constitutes the combination of the reverse enteric polymer and a part of the antacid and the external phase contains other part of the antacid, then the amount of antacid in the internal phase can vary from about 1 to 5% by weight and the amount of antacid present in the external phase can vary from about 10% to 40%, preferably, 25% by weight of the solid dosage form.

The components of each composition were premixed or blended prior to extrusion. The resulting mixture was blended and then screened through a sieve, for eg, No. 20 (0.85 mm) US standard sieve. The mixture was hot melt extruded to obtain an internal phase. This internal phase was optionally, coated with a coating composition containing a water soluble and alcohol dose-dumping resistance polymer, such as polyvinyl alcohol, hydroxyethyl cellulose, hydroxyethylmethyl cellulose, hydroxypropylmethyl cellulose, sodium alginate, pregelatinized starch, hydroxypropyl starch, alginic acid, sodium carboxymethyl cellulose, sodium starch glycolate, ethyl cellulose and like. The polyvinyl alcohol may be present in the form of various grades such as Opadry® II clear 88 F590007: Polyvinyl alcohol, polyethylene glycol and polysorbate 80, Opadry® II clear 85 F19250: Polyvinyl alcohol, polyethylene glycol and polysorbate 80 and talc and the like. The sodium starch glycolate may be present in various grades but not limited to type A low viscosity, type C high viscosity and the like.

In another embodiment, the internal phase itself contains the drug susceptible to abuse, reverse enteric polymer, part of the antacid such as an alkalizer, water soluble and alcohol dose-dumping resistance polymer. The internal phase so formed is further mixed with part of the antacid and may be converted into a capsule filled with the mixture of internal phase and external phase, or the mixture may be converted into a compressed tablet.

According to one specific aspect, the present invention provides an abuse deterrent immediate release biphasic matrix solid dosage form comprising:
 a drug susceptible to abuse and a release inhibiting agent,
 the release inhibiting agent consisting of a combination of
  at least two polymers and an antacid wherein at least one first polymer is a reverse enteric polymer, and at least one second polymer is an alcohol dose-dumping resistance polymer,
 wherein the reverse enteric polymer and a part of the antacid are present in amounts such that when more than one unit of the dosage form are tested for in-vitro dissolution in 500 ml, of 0.01N HCl, Type II USP apparatus (Paddle) rotating at a speed of 50 rpm, the release is inhibited as compared to the immediate release of drug from a single units in 2 hours when a single unit of the dosage form is tested.

According to another aspect, the present invention provides an abuse deterrent immediate release biphasic matrix solid dosage form comprising:
 a drug susceptible to abuse and a release inhibiting agent,
 the release inhibiting agent consisting of a combination of
  at least two polymers and an antacid wherein at least one first polymer is a reverse enteric polymer, and at least one second polymer is alcohol dose-dumping resistance polymer,
 wherein the reverse enteric polymer and the antacid are present in amounts such that when more than three units of the dosage form are tested for in-vitro dissolution in 500 ml of 0.01N HCl, Type II USP apparatus (Paddle) rotating at a speed of 50 rpm, the release is inhibited as compared to the immediate release of drug from a single units in 2 hours when a single unit of the dosage form is tested.

The present invention can be said to provide a single method for resolving multiple modes of abuse immediate release biphasic matrix solid dosage form comprising a drug susceptible to abuse, the multiple modes of abuse including
 a. intentional abuse of overdosing or multiple unit administration by an addict or by a subject having suicidal intention,
 b. intentional abuse of extraction from multiple unit administration by an addict or by a subject having suicidal intention
 c. unintentional or accidental overdosing,
 d. concomitant alcohol consumption and resultant drug-alcohol interaction the method comprising:
  providing an abuse deterrent immediate release solid dosage form comprising a drug susceptible to abuse and a release inhibiting agent,
  the release inhibiting agent consisting of a combination of at least two polymers and an antacid wherein at least one first polymer is a reverse enteric polymer, and at least one second polymer is alcohol dose-dumping resistance polymer such that when the prescribed dose in a single unit of the immediate release solid dosage form is administered, the drug is released at a desired rate for quick onset of action, however if more than one unit of the immediate release solid dosage form are administered, the release of the drug is suppressed; or when a single unit of the immediate release dosage form is administered with concomitant alcohol consumption, the drug is released at a reduced rate as compared to the rate of release from a single unit of the immediate release dosage form in a subject who has not consumed alcohol;

when an abuser attempts to extract the drug from multiple units using alcohol or soft drinks, composition provides a barrier to extraction when an abuser attempts to extract the drug from multiple units via nasal or parental route.

The abuse deterrent immediate release solid dosage form according to the present invention provides resistance to tampering by either an oral, nasal or parenteral route. An abuser when attempts to tamper the dosage form by oral route, being an immediate release dosage form, abuser may ingest more than the prescribed number of units with the aim of achieving high. The inventors have demonstrated that the dosage form provides resistance to tampering by multiple pill administration. If an abuser intends to tamper the biphasic matrix type of embodiments of the multiple units of the solid dosage form of the present invention by crushing and destroying its configuration or by nasal or parenteral means, it was surprisingly found that the dosage form provided resistance to such abuse by not releasing the drug either in the nasal fluids or in aqueous medium, respectively. Particularly, resistant to such abuse are embodiments where the drug is present as a solid solution or solid dispersion in the intragranular phase containing the reverse enteric polymer. The solid solution or solid dispersion of the drug with the reverse enteric polymer may be achieved by any techniques known in the art such as hot melt extrusion, hot melt granulation, or spray drying a solution of the drug and reverse enteric polymer in a suitable solvent. In one specific embodiment, a hot melt extrusion process was employed for achieving the solid solution or solid dispersion of drug and the reverse enteric polymer. In one specific embodiment, the method includes steps of: (a) mixing drug, with a reverse enteric polymer at a temperature sufficiently high to soften or melt the polymer and to melt or dissolve the drug in the polymer, thereby forming a dispersion or solution of drug; and (b) allowing the dispersion or solution to cool. The molten mass may be cooled and then sifted to desirable size and mixed with other excipients, and converted into a solid dosage form. It is possible to incorporate a part of the alkalizer in the dispersion or solution formation step, wherein the drug, reverse enteric polymer and the part of the alkalizer are present in the intragranular phase. This phenomenon was observed when the solid dosage form was tested for its tamper resistance in the acidic media such as citric acid, it provided a lesser dissolution indicating that the solid dosage form having alkalizer in the intragranular phase presents a better control over the resistance to tampering. Incorporation of part of the alkalizer in the intragranular phase, also creates difficulty for the abuser to separate the drug, reverse enteric polymer from the alkalizer, as these are agglomerated together to form particles.

In yet another aspect, the present invention provides an abuse deterrent immediate release biphasic matrix solid dosage form comprising:

a drug susceptible to abuse and a release inhibiting agent, the release inhibiting agent consisting of a combination of at least two polymers and an antacid wherein at least one first polymer is a reverse enteric polymer, and at least one second polymer is alcohol dose-dumping resistance polymer, wherein the antacid is an H2 antagonist.

The present invention provides a method of achieving deterrence to an abuse, wherein the abuse is effected by ingestion of more than prescribed number of units of the solid dosage form, the abuse being either intentional or unintentional. The solid dosage form according to one of the embodiments of the present inventio was tested for pharmacokinetic parameters such as vplasma concentration levels by orally administering more than prescribed number of units such as three. It was found that there was a reduction in the maximum plasma concentration ($C_{max}$) when three units of the solid dosage form were administered as compared to the expected $C_{max}$. Expected $C_{max}$ is the plasma level theoretically achieved if three tablets of test product were ingested. This shows that the immediate release biphasic matrix solid dosage form of the present invention provides deterrence to abuse via administration of more than the prescribed number of units. The reduced $C_{max}$ would provide deterrence to the abuser who attempts to abuse the active ingredient and achieve 'high' by taking more than prescribed number of units of the solid dosage form concurrently.

While the present invention is disclosed generally above, additional aspects are further discussed and illustrated with reference to the examples below. However, the examples are presented merely to illustrate the invention and should not be considered as limitations thereto.

Examples 1 to 5

TABLE 1

| | Immediate release biphasic matrix solid dosage form of Example 1-5 | | | | | |
|---|---|---|---|---|---|---|
| | | Quantity mg/Tablet Examples | | | | |
| | Ingredient | 1 | 2 | 3 | 4 | 5 |
| Intragranular phase | Tapentadol HCl | 17.40 | 17.40 | 17.40 | 11.60 | 11.60 |
| | Methyl methacrylate butyl methacrylate- dimethylaminoethyl methacrylate copolymer (Eudragit ® E PO) | 120.0 | 120.0 | 120.0 | 80.0 | 80.0 |

TABLE 1-continued

Immediate release biphasic matrix solid dosage form of Example 1-5

|  | Ingredient | | | | | |
|---|---|---|---|---|---|---|
| | Hydroxypropyl methyl cellulose | — | — | — | 16.0 | — |
| | Poly vinyl alcohol* | — | — | — | — | 16.0[2] |
| | Poly vinyl alcohol** | — | — | — | 6.8[1] | — |
| Granules of second drug | Acetaminophen | — | — | — | 325.0 | 325.0 |
| | Polyethylene glycol 400 | — | — | — | 5.0 | — |
| | Microcrystalline cellulose | — | — | — | 47.0 | 47.0 |
| | Pregelatinized starch | — | — | — | 25.0 | 25.0 |
| | Sodium starch glycolate | — | — | — | 15.0 | 15.0 |
| | Polyvinyl pyrrolidone | — | — | — | 8.0 | 8.0 |
| Extragranular | Sodium bicarbonate | 560.0 | 560.0 | 280.0 | 280.0 | 280.0 |
| | Magnesium oxide | — | — | 50.0 | 50.0 | 50.0 |
| | Silicified Microcrystalline cellulose | 298.0 | 293.0 | 293.0 | 149.6 | 161.4 |
| | Crospovidone | 30.00 | 30.0 | 30.0 | — | — |
| | Talc | 7.30 | 7.30 | 7.30 | — | — |
| | Magnesium Stearate | 7.30 | 7.30 | 7.30 | 6.0 | 6.0 |

|  | | Quantity % w/w Examples | | | | |
|---|---|---|---|---|---|---|
| | Ingredient | 1 | 2 | 3 | 4 | 5 |
| Intragranular phase | Tapentadol HCl | 1.67 | 1.68 | 2.16 | 1.13 | 1.13 |
| | Methyl methacrylate butyl methacrylate-dimethylaminoethyl methacrylate copolymer (Eudragit® E PO) | 11.53 | 11.59 | 14.9 | 7.8 | 7.80 |
| | Hydroxypropyl methyl cellulose | — | — | — | 1.56 | — |
| | Poly vinyl alcohol* | — | — | — | — | 1.6[2] |
| | Poly vinyl alcohol** | — | — | — | 0.66[1] | — |
| Granules of second drug | Acetaminophen | — | — | — | 31.7 | 31.7 |
| | Polyethylene glycol 400 | — | — | — | 0.48 | — |
| | Microcrystalline cellulose | — | — | — | 4.58 | 4.6 |
| | Pregelatinized starch | — | — | — | 2.43 | 2.4 |
| | Sodium starch glycolate | — | — | — | 1.46 | 1.5 |
| | Polyvinyl pyrrolidone | — | — | — | 0.78 | 0.8 |
| Extragranular phase | Sodium bicarbonate | 53.84 | 54.1 | 34.8 | 27.3 | 27.3 |
| | Magnesium oxide | — | — | 6.21 | 4.87 | 4.9 |
| | Silicified Microcrystalline cellulose | 28.65 | 28.3 | 36.4 | 14.6 | 15.7 |
| | Crospovidone | 2.88 | 2.89 | 3.7 | — | — |
| | Talc | 0.70 | 0.70 | 0.9 | — | — |
| | Magnesium Stearate | 0.70 | 0.70 | 0.9 | 0.58 | 0.58 |

*Opadry ® II clear 88 F590007: Polyvinyl alcohol, polyethylene glycol and polysorbate 80
**Opadry ® II clear 85 F19250: Polyvinyl alcohol, polyethylene glycol and polysorbate 80 and talc
[1]polyvinyl alcohol is present in the form of coating in the drug reverse enteric polymer granules
[2]polyvinyl alcohol is present in the form of admixture in the drug reverse enteric polymer granules Examples 1-3 were prepared as follows:

Tapentadol hydrogen chloride, representing a drug susceptible to abuse and methyl methacrylate butyl methacrylate-dimethyl aminoethyl methacrylate copolymer (Eudragit® EPO) and other intragranular excipients were sifted through 30 # sieve. The mixture was extruded and the extrudates milled and shifted through #20 to obtain granule. The granules were blended with extragranular excipients and subjected to compression using suitable shaped punches to obtain tablets.

Example 4 was prepared as follows:

Tapentadol hydrogen chloride, Methyl methacrylate butyl methacrylate-dimethylaminoethyl methacrylate copolymer (Eudragit® EPO), Hypromellose (Methocel® E-5 LV premium) and Polyethylene glycol 4000 were sifted through 30 # and mixed. The mixture was extruded in a hot melt extruder. Extrudates so obtained were milled and shifted through 20 # sieve. Coating dispersion was prepared by the addition of Opadry II clear 85F19250 in the vortex of purified water with stirring for 45 minutes. Then milled extrudes were coated with n in Glatt coating machine with top spray setup to obtain the coated Tapentadol HCl extrudates.

Acetaminophen, Microcrystalline cellulose (Avicel® PH 101), pregelatinized starch (LYCATAB-PGS®) and Sodium Starch Glycolate (Explotab®) were co-sifted through suitable mesh. Then sifted material was transferred to Rapid mixer granulator and dry mixed for 10 minutes with suitable impeller and chopper setting. Binder solution was prepared by adding Povidone (Plasdone® K-29/32) to the vortex of suitable quantity of purified water under stifling. Granules were prepared with the dry mixed materials and the binder solution, in a rapid mixer granulator suitable impeller and chopper setting. Then wet granules were milled in clit mill with suitable screen. The wet milled granules were dried in fluid bed drier at suitable temperature. Then dried granules were milled in clit mill with suitable screen and sift the milled granules through suitable mesh to obtain the Acetaminophen granules.

The coated Tapentadol HCl extrudates were mixed with Acetaminophen granules, sodium bicarbonate, magnesium Oxide and silicified microcrystalline cellulose. It was then blended in a suitable blender followed by lubrication with Magnesium stearate. Then the blend was compressed to obtain tablets using suitable shaped punches.

Example 5 was prepared as follows:

Tapentadol hydrogen chloride, Methyl methacrylate butyl methacrylate-dimethylaminoethyl methacrylate copolymer (Eudragit® EPO) and Opardy® II clear 88 F590007 were sifted through suitable sieve and mixed The mixture was extruded in a hot melt extruder and the extrudates were milled and shifted through suitable sieve to obtain Tapentadol extrudates.

Acetaminophen, Microcrystalline cellulose (Avicel® PH 101), Pregelatinized starch (LYCATAB-PGS®) and Sodium Starch Glycolate (Explotab®) were co-sifted through suitable mesh. Then sifted material was transferred to Rapid mixer granulator and dry mixed for 10 minutes with suitable impeller and chopper setting. Binder solution was prepared by adding Povidone (Plasdone® K-29/32) to the vortex of suitable quantity of purified water under stifling. Granules were prepared with the dry mixed materials and the binder solution, in a rapid mixer granulator at suitable impeller and chopper setting. The wet granules were milled in clit mill with suitable screen. The wet milled granules were dried in fluid bed drier at suitable temperature. Then dried granules were milled in clit mill with suitable screen and sift the milled granules through suitable mesh.

Tapentadol extrudates, Acetaminophen granules, Sodium bicarbonate, Magnesium Oxide and Silicified Microcrystalline cellulose were blended in a suitable blender followed by lubrication with Magnesium stearate. Then blend was compressed to obtain tablets using suitable shaped punches.

The tablets of Examples 1-5 were tested for in-vitro dissolution in 500 ml, 0.01N HCl, in Type II USP apparatus (Paddle) rotating at a speed of 50 rpm. Single as well as more than single unit were placed together in the dissolution bath to check the dissolution release of the drug. The results are shown in Table 2 and in FIGS. 1-5.

TABLE 2

In vitro release of 'N' number of units of Examples 1-5

% drug released

| | Example 1 | | | | | Example 2 | | Example 3 | | Example 4 | | Example 5 | |
|---|---|---|---|---|---|---|---|---|---|---|---|---|---|
| Time (Min) | N = 1 (A)* | N = 2 (B*) | N = 3 (B*) | N = 5 (B*) | N = 7 (B*) | N = 1 (A)* | N = 3 (B*) | N = 1 (A)* | N = 3 (B*) | N = 1 (A)* | N = 3 (B*) | N = 1 (A)* | N = 3 (B*) |
| 0 | 0 | 0 | 0 | 0 | 0 | 0 | 0 | 0 | 0 | 0 | 0 | 0 | 0 |
| 10 | 99 | 64 | 42 | 33 | 23 | 99 | 45 | 71 | 40 | 75 | 38 | 64 | 35 |
| 20 | 103 | 70 | 46 | 36 | 27 | 104 | 52 | 86 | 46 | 89 | 45 | 96 | 45 |
| 30 | 106 | 74 | 50 | 41 | 34 | 105 | 55 | 90 | 48 | 92 | 49 | 96 | 50 |
| 45 | 106 | 76 | 52 | 42 | 35 | 104 | 56 | 93 | 49 | 95 | 52 | 98 | 56 |
| 60 | 106 | 77 | 52 | 42 | 37 | 105 | 57 | 93 | 50 | 95 | 54 | 100 | 59 |

*A = % release when N = 1

It was found that the release inhibiting agent function to release the drug rapidly in gastric fluids when a single unit is tested but inhibited the release of the drug in gastric fluids when more than the prescribed number of units of the dosage form were tested.

The percent inhibition of release was calculated as follows:

*% inhibition of release with $N$ units $= (A-B/A) \times 100$ where

A = % release when N=1 and B = % release with N units

The % inhibition of release with N units for examples 1 to 5 is shown in Table 3.

TABLE 3

Percent inhibition of release by Examples 1-5

% inhibition of release with N units*

| | Example 1 | | | | Example 2 | Example 3 | Example 4 | Example 5 |
|---|---|---|---|---|---|---|---|---|
| Time (Min) | N = 2 | N = 3 | N = 5 | N = 7 | N = 3 | N = 3 | N = 3 | N = 3 |
| 10 | 35 | 57 | 67 | 77 | 55 | 44 | 49 | 45 |
| 20 | 32 | 55 | 65 | 74 | 50 | 47 | 49 | 53 |
| 30 | 30 | 52 | 61 | 68 | 48 | 47 | 47 | 48 |
| 45 | 28 | 51 | 60 | 67 | 46 | 47 | 45 | 43 |
| 60 | 27 | 51 | 60 | 65 | 46 | 46 | 43 | 41 |

These examples illustrated the abuse deterrent immediate release solid dosage form of the present invention comprising a drug susceptible to abuse and a release inhibiting agent wherein the release inhibiting agent is a combination of polymer and an alkalizer and wherein the polymer functions as a release rate controlling polymer above a critical pH but has little rate controlling ability below the critical pH and is present in admixture with the drug in one phase and the alkalizer is present in another phase (biphasic matrix type). Thus it was observed that when two or more units of the biphasic matrix type embodiments of the present invention were orally administered, the release was inhibited as compared to the release when a single unit of the dosage form was orally administered.

In the particular, in the illustrative examples 1-5, the percent inhibition observed was from about 30% to about 80% at 10, 20, 30, 45 and 60 minutes. When N was 2, the percent inhibition in the illustrative example was from about 30 to 35%. The percent inhibition ranged from about 40 to about 60%, when N was 3, from about 60 to 70% when N was 5 and from about 65 to about 80% when N was 7.

As dosage forms intended for quick onset of action are given a number of times a day as compared to slow release forms that are given at a lower frequency for example once-a-day, they contain a lower amount of drug than in the extended release form. An abuser will want to receive higher amounts by taking multiple pills. Therefore, the percent of prescribed dose that an abuser will release at 10 min. and 60 min. for absorption by taking multiple units of the dosage form was calculated. The prescribed dose is the amount contained in a single unit of the dosage form. Table 4 shows the results for Examples 1-5.

TABLE 4

Estimated percent prescribed dose release at 10 minutes and 60 minutes upon abuse by multiple unit administration of the biphasic matrix type dosage form of the present invention

| Examples | $D_{10}$* | | | | | $D_{60}$** | | | | |
|---|---|---|---|---|---|---|---|---|---|---|
| | N = 1 | N = 2 | N = 3 | N = 5 | N = 7 | N = 1 | N = 2 | N = 3 | N = 5 | N = 7 |
| 1 | 99 | 128 | 126 | 165 | 161 | 106 | 154 | 156 | 210 | 259 |
| 2 | 99 | — | 135 | — | — | 105 | — | 171 | — | — |
| 3 | 71 | — | 120 | — | — | 93 | — | 150 | — | — |
| 4 | 75 | — | 76 | — | — | 95 | — | 162 | — | — |
| 5 | 64 | — | 70 | — | — | 100 | — | 177 | — | — |

*$D_{10}$ = Percent prescribed dose released in 10 minutes = (Total amount released/amount in prescribed number of units of the dosage form) × 100

**$D_{60}$ = Percent prescribed dose released in 60 minutes = (Total amount released/amount in prescribed number of units of the dosage form) × 100

Example 5A

Example 5A demonstrates the ability of the immediate release solid dosage form to provide resistance to drug release in presence of alcohol.

This embodiment provides the solid dosage form that is alcohol resistant. Immediate release solid dosage forms according to the Example 4 and Example 5 were tested for the in vitro dissolution in the presence and absence of alcohol. The tablets were tested for in-vitro dissolution in 500 ml, 40% v/v ethanolic solution, in Type II USP apparatus (Paddle) rotating at a speed of 50 rpm.

Example 4 and Example 5 represent the embodiment of the present invention wherein the abuse deterrent immediate release solid dosage form comprises a drug susceptible to abuse and a release inhibiting agent, the release inhibiting agent consisting of a combination of a reverse enteric polymer and an alcohol dose-dumping resistance polymer.

The following data shows that when a single unit of the immediate release dosage form is administered with concomitant alcohol consumption, the drug is released at a reduced rate as compared to the rate of release from a single unit of the immediate release dosage form in a subject who has not consumed alcohol.

TABLE NO. 5

Results of the In vitro release of the drug from the single unit of the dosage form in the presence and absence of 40% ethanolic medium

| | Example 1 (N = 1) | | Example 4 (N = 1) | | Example 5 (N = 1) | |
|---|---|---|---|---|---|---|
| | Dissolution medium | | | | | |
| Time in minutes | with 40% alcohol | without alcohol | with 40% alcohol | without alcohol | with 40% alcohol | without alcohol |
| 10 | 68 | 0 | 22 | 75 | 22 | 64 |
| 20 | 85 | 99 | 41 | 89 | 39 | 96 |
| 30 | 94 | 103 | 53 | 92 | 49 | 96 |
| 45 | 96 | 106 | 70 | 95 | 59 | 98 |
| 60 | 100 | 106 | 77 | 95 | 64 | 100 |

The results in the above table indicate that when an abuser attempts to extract the drug from multiple units using alcohol or a user unintentionally takes substantial quantity of alcohol, the composition provides a barrier to extraction or to alcohol dose-dumping.

Example 5B

Example 5B demonstrates the ability of the immediate release solid dosage form to provide resistance to extraction by use of acidic beverages that may be used by an abuser.

Solid dosage form of the Example 5 represents an embodiment of the present invention wherein the abuse deterrent immediate release solid dosage form comprises: a drug susceptible to abuse and a release inhibiting agent, the release inhibiting agent consisting of a combination of a reverse enteric polymer and alcohol dose-dumping resistance polymer such as polyvinyl alcohol and antacid. The Solid dosage form of Example 5 was evaluated for ability to resist the abuse by techniques such as extraction of the drug using acidic beverages such as soft drinks like, for eg. Coca Cola® and Sprite®. In order to evaluate this, multiple units of the solid dosage form were subjected to in vitro release in 500 ml of the soft drink and the release was measured for 1 hour.

TABLE NO 6

Results of Evaluation of the ability of the immediate release solid dosage form of Example 5 (Five units) to provide resistance to extraction by soft drinks by an abuser

| | % In vitro dissolution of Five Immediate release solid dosage form of Example 5 | |
|---|---|---|
| Time in minutes | Coca cola ® | Sprite ® |
| 5 | 32 | 49 |
| 10 | 40 | 64 |
| 15 | 44 | 69 |
| 30 | 48 | 75 |
| 45 | 51 | 76 |
| 60 | 53 | 77 |

The results from EXAMPLE 5A and EXAMPLE 5B illustrate that when an abuser attempts to extract the drug from multiple units of the immediate release solid dosage form of the present invention using alcohol or soft drinks, dosage form shows ability to provide a barrier to extraction.

Example 6 and Example 6 A

TABLE 7

Immediate release solid dosage form of Example 6 and Example 6A

| Description of the dosage form | Ingredients | Example 6 | | Example 6 A | |
|---|---|---|---|---|---|
| | | Mg per tablet | % by weight | Mg per tablet | % by weight |
| Drug 'reverse enteric polymer' granules | model drug (Tapentadol HCl) | 11.60 | 1.45 | 11.60 | 1.70 |
| | Methyl methacrylate butyl methacrylate-dimethylaminoethyl methacrylate copolymer | 80.00 | 10.0 | 80.00 | 11.76 |
| | Polyvinyl alcohol** | 16.00 | 2.0 | 16.00 | 2.35 |
| | Magnesium Oxide: base | — | — | 10.00 | 1.47 |
| Extragranular | Sodium bicarbonate | 280.00 | 35.0 | 280.00 | 41.17 |
| | Magnesium Oxide | 50.00 | 6.25 | — | — |
| | Silicified Microcrystalline cellulose | 269.9 | 33.7 | 228.4 | 33.58 |
| | Crospovidone | 70.00 | 8.75 | 40.00 | 6.88 |
| | Colloidal Silicon Dioxide | 8.50 | 1.06 | — | — |
| | Talc | 7.00 | 0.87 | 7.00 | 1.02 |
| | Magnesium Stearate | 7.00 | 0.87 | 7.00 | 1.02 |

**Opadry ® II Clear 88F590007: polyvinyl alcohol;

The extrudates were prepared by hot melt extrusion. All the ingredients of the hot melt extrusion stage were sifted through a suitable sieve. The sifted ingredients were mixed and extrudates were prepared using hot melt extruder. The extrudates were milled and sifted through sieve. The extrudates were lubricated and further dry mixed with sodium bicarbonate, magnesium oxide, silicified microcrystalline cellulose, crospovidone and the mixture is compressed into tablet.

The single and multiple units of the solid dosage form of Example 6 and Example 6A were subjected to in vitro dissolution to evaluate ability of the solid dosage form to provide multiple pill abuse. For this, single and three tablets were placed in the dissolution vessel having 500 ml 0.01 N HCL. Type II USP dissolution apparatus rotating at a speed of about 50 rpm, was used. The dissolution was measured for 60 minutes. Following table provides the results of the dissolution test.

TABLE NO 8

Results of the in-vitro release of the drug from the single and three units of the dosage form of Example 6 and Example 6A

| Time in minutes | Example 6 | | Example 6 A | |
|---|---|---|---|---|
| | N = 1 | N = 3 | N = 1 | N = 3 |
| 5 | 52 | 38 | 40 | 32 |
| 10 | 74 | 45 | 52 | 36 |
| 15 | 85 | 50 | 61 | 41 |
| 30 | 92 | 58 | 82 | 49 |
| 45 | 94 | 61 | 91 | 54 |
| 60 | 94 | 63 | 95 | 57 |

It can be seen that the reverse enteric polymer, Methyl methacrylate butyl methacrylate-dimethylaminoethyl methacrylate copolymer and the antacid, which is a mixture of magnesium oxide and sodium bicarbonate, are present in amounts such that when two or more units of the dosage form are tested for in-vitro dissolution in 500 ml, 0.01N HCl, in Type II USP apparatus (Paddle) rotating at a speed of 50 rpm, the release is inhibited as compared to the immediate release of atleast 80±5% of drug in a single unit of the dosage form in 1 hour when a single unit of the dosage form is tested.

Example 6B

TABLE 9

Immediate release solid dosage form of Example 6B

| | Ingredients | mg/Tab | % by weight of tab |
|---|---|---|---|
| Intragranular phase | Tizanidine hydrochloride | 2.3 | 0.27 |
| | Lactitol monohydrate | 12.3 | 1.45 |
| | Aminomethacrylate copolymer (Eudragit ® EPO) | 100. | 11.76 |
| | Polyvinyl alcohol** | 20. | 2.35 |
| | Hydrochloric Acid | 1.4 | 0.2 |
| Extragranular phase | Sodium bicarbonate Powder | 280.0 | 32.9 |
| | Magnesium Oxide Light | 50. | 5.9 |
| | Silicified Microcrystalline cellulose (Prosolv SMCC 90) | 291.5 | 34.3 |
| | Crospovidone | 70.0 | 8.2 |
| | Colloidal Silicon Dioxide | 8.5 | 1 |
| Lubrication stage | Talc | 7.0 | 0.82 |
| | Magnesium Stearate | 7.0 | 0.82 |

**Opadry ® II Clear 88F590007-Polyvinyl alcohol, polyethylene glycol and polysorbate 80.
Example 6B was prepared as follows:

Drug susceptible to alcohol and Lactitol monohydrate salt were sifted, mixed and further granulated with hydrochloric acid. The aminomethacrylate copolymer and polyvinyl alcohol were sieved and mixed with the granulation blend prepared before. This mixture was then extruded by hot melt extrusion. The extrudes were further milled and mixed with sodium bicarbonate powder, magnesium oxide light, silicified microcrystalline cellulose, crospovidone and colloidal silicon dioxide, talc and magnesium stearate and tablets were compressed.

Dissolution was carried out in 500 ml of 0.01N HCl in a Type-IL USP apparatus at a rotating speed of 50 rpm in a peak vessel. Abuse deterrence was compared by checking the decrease in the percentage release of the drug from one unit of the solid dosage form compared to more than the prescribed number of units for eg 3 units. The results of the dissolution study are given below:

TABLE 10

In vitro dissolution of the solid dosage form of Example 6B

| | % Drug Release [Mean] | |
|---|---|---|
| Time in minutes | Number of units tested N = 1 | Number of units tested N = 3 |
| 5 | 33 | 12 |
| 10 | 63 | 21 |
| 15 | 81 | 29 |
| 20 | 90 | 36 |
| 30 | 97 | 46 |
| 45 | 98 | 58 |
| 60 | 99 | 65 |

The tablets prepared according to this example, were subjected to pharmacokinetic study. The details of the study and the results are provided in Example 18.

Example 7 and Example 8

TABLE 11

Immediate release solid dosage form of Example 7 & Example 8

| Description of dosage form | Ingredients | Example 7 mg per tablet | Example 7 % by weight | Example 8 mg per tablet | Example 8 % by weight |
|---|---|---|---|---|---|
| Intra-granular phase | model drug (Tapentadol HCl) | 11.6 | 1.1 | 11.6 | 1.11 |
| | Methyl Methacrylate and Diethylaminoethyl Methacrylate copolymer dispersion * | 80.0 | 7.47 | 100.0 | 9.61 |
| | Polyvinyl alcohol** | 16.00 | 1.49 | 25.0 | 2.40 |
| | Tartaric acid | — | — | 2.2 | 0.21 |
| | Magnesium Oxide | — | — | 10.0 | 0.96 |
| Granules of second drug | Acetaminophen granules | 420.00 | 39.25 | NA | — |
| | Acetaminophen granules (Compresso PAP ® 90CPF) | NA | — | 360.0 | 34.61 |
| extra-granular | Sodium bicarbonate | 280.0 | 26.2 | 280.0 | 26.92 |
| | Magnesium Oxide | 50.0 | 4.7 | NA | — |
| | Silicified Microcrystalline cellulose (Prosolv SMCC 90) | 168.4 | 15.74 | 207.2 | 19.92 |
| | Crospovidone | 20.0 | 1.86 | 20.0 | 1.9 |
| | Silicon dioxide | 10.0 | 0.93 | 10.0 | 0.9 |
| | Talc | 7.0 | 0.65 | 7.0 | 0.7 |
| | Magnesium Stearate | 7.0 | 0.65 | 7.0 | 0.7 |

* Methyl Methacrylate and Diethylaminoethyl Methacrylate copolymer dispersion (Kollicoat ® Smart Seal 30D) in dried form
**Polyvinyl alcohol: Opadry ® II clear 85 F59007

The ingredients namely, tapentadol, Methyl Methacrylate and diethylaminoethyl methacrylate copolymer, polyvinyl alcohol, tartaric acid and magnesium oxide (in case of Example 8) were sifted and mixed. The blend was subjected to hot melt extrusion to prepare the extrudates. The extrudates were milled and sifted and mixed with the acetaminophen granules, sodium bicarbonate, magnesium oxide, silicified microcrystalline cellulose, crospovidone, pregelatinized starch. They were lubricated with talc and magnesium stearate and compressed into tablets.

The tablets of Example 7 and Example 8 were subjected to in vitro dissolution in 500 ml of 0.01 N HCL using type II apparatus at a rotating speed of 50 rpm. Below are the results:

TABLE 12

Results of in vitro release of the drug from the single and three units of the dosage form of Example 7 and Example 8

| Time in minutes | EXAMPLE 7 N = 1 | EXAMPLE 7 N = 3 | EXAMPLE 8 N = 1 | EXAMPLE 8 N = 3 |
|---|---|---|---|---|
| 5 | 41 | 29 | 26 | 9 |
| 10 | 60 | 41 | 36 | 16 |
| 15 | 74 | 48 | 45 | 20 |
| 30 | 90 | 57 | 64 | 31 |
| 45 | 95 | 61 | 73 | 37 |
| 60 | 97 | 64 | 81 | 40 |

The tablets of Example 7 and example 8, were further subjected to in vitro dissolution using 500 ml of 0.01N HCl with 720 mg citric acid using type II USP apparatus at a rotating speed of 50 rpm. Below are the results.

TABLE 13

Results of the In vitro release of the drug from three units of the dosage form in 500 ml of 0.01N HCl with 720 mg citric acid

| Time in minutes | EXAMPLE 7 N = 3 | EXAMPLE 8 N = 3 |
|---|---|---|
| 5 | 27 | 19 |
| 10 | 44 | 29 |
| 20 | 52 | 36 |
| 30 | 73 | 48 |
| 45 | 85 | 56 |
| 60 | 89 | 63 |

Example 9 and Example 10

TABLE 14

Immediate release solid dosage form of Example 9 and 10

| Description of dosage form | Ingredients | Example 9 mg per tablet | Example 9 % by weight | Example 10 mg per tablet | Example 10 % by weight |
|---|---|---|---|---|---|
| Drug 'reverse enteric polymer' granule | model drug (Tapentadol HCl) | 11.6 | 1.1 | 11.60 | 1.06 |
| | Methyl Methacrylate and Diethylaminoethyl Methacrylate copolymer dispersion * | 100.0 | 9.2 | 100.0 | 9.17 |
| | Polyvinyl alcohol** | 25 | 2.3 | 25.0 | 2.29 |
| | Tartaric acid | 2.2 | 0.2 | 2.22 | 0.20 |
| | Magnesium Oxide | 10.0 | 0.9 | 10.00 | 0.91 |
| Granules of second drug | Acetaminophen granules | 360 | 33.0 | 360 | 33.0 |
| extra-granular | Sodium bicarbonate | 280 | 25.7 | 280 | 25.7 |
| | Polyethylene oxide | 90 | 8.2 | 90 | 8.25 |
| | Silicified Microcrystalline cellulose | 97.2 | 8.9 | 97.2 | 8.91 |
| | Crospovidone | 20 | 1.8 | 20 | 1.83 |
| | Sodium starch glycolate-Type A | 70 | 6.4 | NA | — |
| | Sodium starch glycolate-Type C | NA | — | 70 | 6.42 |

TABLE 14-continued

Immediate release solid dosage form of Example 9 and 10

| Description of dosage form | Ingredients | Example 9 | | Example 10 | |
|---|---|---|---|---|---|
| | | mg per tablet | % by weight | mg per tablet | % by weight |
| | Light anyhydrous silicic acid | 10 | 0.91 | 10 | 0.91 |
| | Talc | 7 | 0.64 | 7 | 0.64 |
| | Magnesium Stearate | 7 | 0.64 | 7 | 0.64 |

\* Methyl Methacrylate and Diethylaminoethyl Methacrylate copolymer dispersion (Kollicoat ® Smart Seal 30D) in dried form
\*\*Polyvinyl alcohol: Opadry ® II clear 85 F59007

The ingredients namely, tapentadol, Methyl Methacrylate and diethylaminoethyl methacrylate copolymer, polyvinyl alcohol, tartaric acid and magnesium oxide (in case of Example 10) were sifted and mixed. The blend was subjected to hot melt extrusion to prepare the extrudates. The extrudates were milled and sifted through suitable sieve. The extrudates were mixed with the acetaminophen granules, sodium bicarbonate, magnesium oxide, silicified microcrystalline cellulose, crospovidone, pregelatinized starch. Lubricated with talc and magnesium stearate and compressed into tablets. The tablets of Example 10A and Example 10 B were subjected to in vitro dissolution in 500 ml of 0.01 N HCL using type II apparatus at a rotating speed of 50 rpm. Below are the results:

TABLE 15

Results of in vitro release of the drug from the single and three units of the dosage form of Example 9 and Example 10

| Time in | EXAMPLE 9 | | EXAMPLE 10 | |
|---|---|---|---|---|
| minutes | N = 1 | N = 3 | N = 1 | N = 3 |
| 5 | 22 | 11 | 21 | 11 |
| 10 | 34 | 16 | 34 | 19 |
| 15 | 45 | 22 | 47 | 21 |
| 30 | 68 | 34 | 71 | 31 |
| 45 | 81 | 40 | 82 | 38 |
| 60 | 90 | 44 | 88 | 42 |

The tablets of Example 10A and example 10 B, were further subjected to in vitro dissolution using 500 ml of 0.01N HCl with 40% alcohol using type II USP apparatus at a rotating speed of 50 rpm. Below are the results.

TABLE 16

Results of the In vitro release of the drug from three units of the dosage form in 500 ml of 0.01N HCl with 40% v/v alcohol

| Time in | EXAMPLE 9 | | EXAMPLE 10 | |
|---|---|---|---|---|
| minutes | N = 1 | N = 3 | N = 1 | N = 3 |
| 5 | 18 | 12 | 8 | 9 |
| 10 | 30 | 21 | 15 | 16 |
| 15 | 40 | 29 | 21 | 22 |
| 30 | 60 | 43 | 31 | 31 |
| 45 | 71 | 52 | 38 | 38 |
| 60 | 77 | 58 | 42 | 42 |

The tablets of the Example 9 were subjected to mechanical tampering. The mechanical tampering was performed by grinding the tablets into a coffee grinder for 20 seconds. The grinding converted the tablet into powder. The powder was subjected to in vitro dissolution in 0.01 N HCL. The results are given below:

TABLE 17

Results of the In vitro release of the drug from three units of the dosage form in 500 ml of 0.01N HCl of intact vs crushed tablets Example 9

| | Sample Type | | |
|---|---|---|---|
| | Intact Tablets | | Crushed Tablets |
| Time in | % Drug Release | | |
| minutes | N = 1 | N = 3 | N = 3 |
| 5 | 22 | 11 | 15 |
| 10 | 34 | 16 | 22 |
| 15 | 45 | 22 | 28 |
| 30 | 68 | 34 | 40 |
| 45 | 81 | 40 | 48 |
| 60 | 90 | 44 | 53 |

It can be seen that in-vitro release of three tablets was suppressed when the tablets were crushed, when compared to in-vitro release of three intact tablets. It is found that although the physical integrity of the tablets is made to lose, the abuse deterrent immediate release solid dosage form of the present invention provided resistance to tampering or misuse.

Example 11

| | | Example 11 | |
|---|---|---|---|
| Description of dosage form | Ingredients | mg per tablet | % by weight |
| Intragranular phase | model drug (Tapentadol HCl) | 11.6 | 1.2 |
| | Methyl Methacrylate and Diethylaminoethyl Methacrylate copolymer dispersion* | 100.0 | 10.3 |
| | Ethyl Cellulose** | 25 | 2.5 |
| | Tartaric acid | 2.2 | 0.22 |
| | Magnesium Oxide | 10.0 | 1.0 |
| | Acetaminophen granules) | 360 | 37.1 |
| Extragranular phase | Sodium bicarbonate | 100 | 10.3 |
| | Magnesium oxide | 50 | 5.15 |
| | Polyethylene oxide | 90.0 | 9.27 |
| | Silicified Microcrystalline cellulose | 107.2 | 11.0 |
| | Crospovidone | 20 | 2.06 |
| | Sodium starch glycolate-Type A | 70 | 7.2 |
| | Light anyhydrous silicic acid | 10 | 1.0 |
| | Talc | 7 | 0.7 |
| | Magnesium Stearate | 7 | 0.7 |

(Kollicoat ® Smart Seal 30D) =
\*Methyl Methacrylate and Diethylaminoethyl Methacrylate copolymer dispersion The ingredients namely, tapentadol, Methyl Methacrylate and diethylaminoethyl methacrylate copolymer, polyvinyl alcohol, tartaric acid and magnesium oxide (in case of Example 10) were sifted and mixed. The blend was subjected to hot melt extrusion to prepare the extrudates. The extrudates were milled and sifted through suitable sieve. The extrudates were mixed with the acetaminophen granules, sodium bicarbonate, magnesium oxide, silicified microcrystalline cellulose, crospovidone, pregelatinized starch. Lubricated with talc and magnesium stearate and compressed into tablets.

The tablets of Example 11 were subjected to in vitro dissolution in 500 ml of 0.01 N HCL using type II apparatus at a rotating speed of 50 rpm. Below are the results:

TABLE 19

Results of in vitro release of the drug from the single and three units of the dosage form of Example 11

| Time in minutes | EXAMPLE 11 N = 1 | EXAMPLE 11 N = 3 |
|---|---|---|
| 5 | 20 | 4 |
| 10 | 30 | 5 |
| 15 | 38 | 6 |
| 30 | 52 | 7 |
| 45 | 63 | 8 |
| 60 | 70 | 8 |

Example 12-Example 13

TABLE 20

Immediate Release solid Dosage form of Example 12 and Example 13

| Description of dosage form | Ingredients | EXAMPLE 12 mg/Tab | EXAMPLE 12 % by weight | EXAMPLE 13 mg/Tab | EXAMPLE 13 % by weight |
|---|---|---|---|---|---|
| Intragranular phase | model drug (Tapentadol HCl) | 11.60 | 1.11 | 11.60 | 1.11 |
| | Methyl methacrylate butyl methacrylate-dimethylaminoethyl methacrylate co-polymer | 100.00 | 9.61 | NA | — |
| | Methyl Methacrylate and Diethylaminoethyl Methacrylate co-polymer dispersion | NA | — | 100.00 | 9.61 |
| | Polyvinyl alcohol | 25.00 | 2.40 | 25.00 | 2.40 |
| | Tartaric acid | 2.22 | 0.21 | 2.22 | 0.21 |
| | Magnesium Oxide | 15.00 | 1.44 | 10.00 | 0.96 |
| Granules of second drug | Acetaminophen granules | 360.00 | 34.61 | 360.00 | 34.61 |
| Extra-granular | Sodium bicarbonate | 280.00 | 26.92 | 280.00 | 26.92 |
| | Silicified Microcrystalline cellulose | 202.2 | 19.44 | 207.2 | 19.9 |
| | Crospovidone | 20.00 | 1.92 | 20.00 | 1.92 |
| | Colloidal silicon dioxide | 10.00 | 0.96 | 10.00 | 0.96 |
| | Talc | 7.00 | 0.67 | 7.00 | 0.67 |
| | Magnesium Stearate | 7.00 | 0.67 | 7.00 | 0.67 |

The ingredients listed in the hot melt extrusion stage were sifted through suitable sieve. The sifted ingredients were mixed and subjected to hot melt extrusion. The extrudates prepared were sifted through suitable sieve. The sieved granules/extrudates were dry mixed in a suitable blender followed by lubrication with ingredients of lubrication stage. The lubricated granules were compressed into tablets.

The tablets of Example 12 and Example 13 were subjected to in vitro dissolution in 500 ml of 0.01N HCl using Type II, USP apparatus (Paddle) rotating at a speed of 50 rpm. The results of the % drug released in tabulated below:

TABLE 21

Results of the In vitro release of the drug from one and three units of the dosage form in 500 ml of 0.01N HCl

| Time in minutes | Example 12 N = 1 | Example 12 N = 3 | Example 13 N = 1 | Example 13 N = 3 |
|---|---|---|---|---|
| 5 | 32 | 15 | 26 | 9 |
| 10 | 45 | 22 | 36 | 16 |
| 15 | 56 | 27 | 45 | 20 |
| 30 | 78 | 38 | 64 | 31 |
| 45 | 90 | 44 | 73 | 37 |
| 60 | 97 | 50 | 81 | 40 |

The results in the above table indicate that when the prescribed dose in a single unit of the immediate release solid dosage form is administered, the drug is released at a desired rate for quick onset of action, however if more than one unit of the immediate release solid dosage form are administered, the rate of release of the drug is inhibited.

The tablets of Example 12 and Example 13 were subjected to in vitro dissolution in 500 ml of 0.01 NHCL with 720 mg of citric acid using Type II, USP apparatus (Paddle) rotating at a speed of 50 rpm. The results of the % drug released in tabulated below:

TABLE NO. 22

Results of the In vitro release of the drug from three units of the dosage form in 500 ml of 0.01N HCl with 720 mg citric acid

| Time in minutes | EXAMPLE 12 (N = 3) % Dissolved | EXAMPLE 13 (N = 3) % Dissolved |
|---|---|---|
| 5 | 30 | 19 |
| 10 | 43 | 29 |
| 20 | 59 | 36 |
| 30 | 77 | 48 |
| 45 | 89 | 56 |
| 60 | 97 | 63 |

Example 14

TABLE 23

Immediate release solid dosage form of Example 14

| Description of dosage form | Ingredients | mg per tablet | % by weight |
|---|---|---|---|
| Intragranular phase | model drug (Tapentadol HCl) | 11.6 | 1.1 |
| | Methyl methacrylate butyl methacrylate-dimethylaminoethyl methacrylate copolymer (Eudragit ® E PO) | 80.0 | 7.5 |
| | Polyvinyl alcohol* | 16.0 | 1.5 |
| | Acetaminophen granules | 420.0 | 39.25 |
| Extragranular | Sodium bicarbonate | 180.0 | 26.16 |
| | Magnesium Oxide | 25.0 | 4.67 |
| | Silicified Microcrystalline cellulose (Prosolv SMCC 90) | 193.4 | 15.6 |
| | Talc | 7.0 | 0.65 |
| | Magnesium Stearate | 7.0 | 0.65 |

**Polyvinyl alcohol: Opadry ® II clear 88 F59007

The tablets of Example 14 were subjected to in vitro dissolution in 500 ml of 0.01N HCl using Type II, USP apparatus (Paddle) rotating at a speed of 50 rpm. The results of the % drug released in tabulated below:

TABLE 24

Results of the In vitro release of the drug from two and four units of the dosage form in 500 ml of 0.01N HCl

| Time in minutes | N = 2 | N = 4 |
|---|---|---|
| 5 | 41 | 33 |
| 10 | 59 | 48 |
| 15 | 75 | 55 |
| 30 | 91 | 65 |
| 45 | 94 | 67 |
| 60 | 99 | 69 |

Example 15

Example 15 illustrates the analysis of the values of the $C_{max}$ obtained during the pharmacokinetic study. The graph shows the number of subjects falling in five % range of reduction in the $C_{max}$. The graphical representation is provided in FIG. 17.

The pharmacokinetic parameters of one of the representative abuse deterrent immediate release solid dosage form were evaluated when administered at prescribed dose and when administered at more than prescribed dose such as, for example, three units.

In order to evaluate this, a randomized open label three treatment, single dose, crossover relative bioavailability and dose proportionality study was carried out under fasting conditions. Eighteen healthy human volunteers were dosed for the study of which fifteen completed the study. The three groups that received the abuse deterrent immediate release solid dosage form, were as follows:

Treatment group A: This group received abuse deterrent immediate release solid dosage form prepared as described in the example 6B.

Treatment group B: This group received three units (more than the prescribed number of units) of the abuse deterrent immediate release solid dosage form prepared as described in the example 6B.

Treatment group C: This group received single (prescribed number of unit) of the solid dosage form prepared in conventional manner, i.e without any abuse deterrent properties.

Post dose blood samples were collected at 0.25, 0.50, 0.75, 1.00, 1.25, 1.50, 1.75, 2.00, 2.50, 3.00, 4.00, 6.00, 8.00, 10.00, and 12.00 hours. The Plasma concentrations obtained at various time points were plotted for all the three group of volunteers. The plasma levels of the group A were compared with the plasma levels of the group B, in a dose proportionate manner.

The percentage reduction in the $C_{max}$ achieved by group B treatment as compared to the $C_{max}$ achieved by group A treatment values multiplied by three i.e (3×A) expected $C_{max}$ (the value of Cmax that would be theoretically achieved if three tablets of test product were taken, as shown in the table below:

TABLE 25

Depicts percentage reduction in the Cmax achieved by group B treatment as compared to the Cmax achieved by group A treatment values multiplied by three

| volunteer no | Expected (3A) | Achieved (B) | % reduction in $C_{max}$*from the expected |
|---|---|---|---|
| 1 | 3906.3 | 2395.4 | 38.68 |
| 2 | 4209 | 4103.4 | 2.509 |
| 3 | 930.9 | 1308.8 | −40.595 |
| 4 | 1291.2 | 995.6 | 22.89 |
| 5 | 2134.5 | 2159.6 | −1.18 |
| 6 | 2984.7 | 2670.7 | 10.52 |
| 7 | 10257 | 7903.3 | 22.947 |
| 8 | 3915.3 | 2543 | 35.050 |
| 9 | 4760.1 | 2136.1 | 55.125 |
| 10 | 5625.9 | 4323.1 | 23.157 |
| 11 | 10925.7 | 7183.8 | 34.25 |
| 12 | 7286.7 | 3126.3 | 57.095 |
| 13 | 494.4 | 360 | 27.184 |
| 14 | 10583.1 | 6182.9 | 41.58 |
| 15 | 10829.4 | 6550.7 | 39.51 |
| Average | 5342.28 | 3596.18 | 32.684 |

*% reduction of $C_{max}$ from expected = ($C_{max}$ expected − $C_{max}$ achieved) * 100/$C_{max}$ expected ie. [(3A − B)*100]/3A The results of the experiment indicate that when one of the embodiments of the invention was tested the actual $C_{max}$ achieved after administration of three tablets of the present invention was lower as compared to the expected $C_{max}$. This shows that the immediate release biphasic matrix solid dosage form of the present invention provides deterrence to abuse via administration of more than the prescribed number of units. The reduced $C_{max}$ would provide deterrence to the abuser who attempts to abuse the active ingredient and achieve 'high' by taking more than prescribed number of units of the solid dosage form concurrently.

Example 16

The intragranular phase was prepared by mixing drug and the reverse enteric polymer and subjecting the mixture to hot melt extrusion. The extrudates were milled and were subjected to X-ray diffraction along with physical mixture of the drug and the reverse enteric polymer, drug alone and the blend of Methyl methacrylate and Diethyl aminoethyl methacrylate copolymer in the powder form and polyvinyl alcohol but without drug (referred to as placebo).

Table No. 26: Composition Details of the Intragranular Phase

Procedure: The specified amounts of tapentadol, Methyl methacrylate and Diethyl aminoethyl methacrylate copolymer in the powder form and polyvinyl alcohol were mixed. The blend was subjected to hot melt extrusion at a temperature of about 155°-1600 C. The extrudates so prepared were milled and sifted through suitable sieve. The milled extrudes were subjected to XRD diffraction. Figure demonstrates that a solid dispersion of tapendadol is obtained.

What is claimed is:

1. An abuse deterrent immediate release biphasic matrix solid dosage form comprising:
    an intragranular phase comprising a mixture of a drug susceptible to abuse and a reverse enteric polymer;
    an extragranular phase;
    and an alkalizer,
    wherein the reverse enteric polymer is a copolymer of methylmethacrylate and diethylaminoethyl methacrylate, and wherein the intragranular phase further comprises a first part of the alkalizer and the extragranular phase comprises a second part of the alkalizer.

2. The abuse deterrent immediate release biphasic matrix solid dosage form according to claim 1
   wherein the drug susceptible to abuse and the reverse enteric polymer are melt extruded to form a solid dispersion characterized by the absence of X-ray diffraction peaks characteristic of the crystalline drug.

3. The abuse deterrent immediate release biphasic matrix solid dosage form according to claim 1, further comprising an alcohol dose dumping resistance polymer located only in the intragranular phase.

4. The abuse deterrent immediate release biphasic matrix solid dosage form according to claim 1, further comprising an alcohol dose dumping resistance polymer located in both the intragranular phase and extragranular phase.

5. The abuse deterrent immediate release biphasic matrix solid dosage form according to claim 1, further comprising an alcohol dose dumping resistance polymer that covers the intragranular phase.

6. The abuse deterrent immediate release biphasic matrix solid dosage form according to claim 5, wherein the alcohol dose dumping resistance polymer is also present in the intragranular phase.

7. The abuse deterrent immediate release biphasic matrix solid dosage form according to claim 6, wherein the alcohol dose dumping resistance polymer is also present in the extragranular phase.

* * * * *